US012245864B2

(12) United States Patent
Funabiki et al.

(10) Patent No.: US 12,245,864 B2
(45) Date of Patent: Mar. 11, 2025

(54) IMAGING DEVICE, OCULAR MOVEMENT DATA PROCESSING SYSTEM, AND CONTROL METHOD

(71) Applicant: J. MORITA MFG. CORP., Kyoto (JP)

(72) Inventors: Kazuo Funabiki, Kobe (JP); Yutaka Ito, Kyoto (JP); Fuyuki Yamada, Kyoto (JP)

(73) Assignee: J. MORITA MFG. CORP., Kyoto (JP)

( * ) Notice: Subject to any disclaimer, the term of this patent is extended or adjusted under 35 U.S.C. 154(b) by 59 days.

(21) Appl. No.: 17/735,538

(22) Filed: May 3, 2022

(65) Prior Publication Data

US 2022/0354414 A1  Nov. 10, 2022

(30) Foreign Application Priority Data

May 10, 2021  (JP) ................................. 2021-079599

(51) Int. Cl.
*H04N 23/45* (2023.01)
*A61B 3/113* (2006.01)
*A61B 5/00* (2006.01)
*H04N 7/18* (2006.01)
*H04N 23/51* (2023.01)

(52) U.S. Cl.
CPC ............ *A61B 5/4023* (2013.01); *A61B 3/113* (2013.01); *H04N 7/183* (2013.01); *H04N 23/45* (2023.01); *H04N 23/51* (2023.01)

(58) Field of Classification Search
CPC ...... A61B 5/4023; A61B 3/113; H04N 23/45; H04N 7/183; H04N 23/51

USPC ........................................................... 348/78
See application file for complete search history.

(56) References Cited

U.S. PATENT DOCUMENTS

| 2003/0086061 | A1  | 5/2003 | Pfleger |
| 2011/0176106 | A1* | 7/2011 | Lewkowski ............. A61B 3/14 351/246 |
| 2016/0165220 | A1* | 6/2016 | Fujimaki ................ G09G 3/001 345/87 |
| 2020/0154025 | A1  | 5/2020 | Wakatsuki |

FOREIGN PATENT DOCUMENTS

| JP |     11225968 A  * |  8/1999 |
| JP |  2001-321342 A   | 11/2001 |
| JP |  2014-104120 A   |  6/2014 |
| JP |    2016-33611 A  |  3/2016 |
| JP |     5981858 B2   |  8/2016 |
| JP |  2018-207453 A   | 12/2018 |

(Continued)

OTHER PUBLICATIONS

Extended European Search Report issued Sep. 29, 2022 in European Patent Application No. 22171887.7, 7 pages.

(Continued)

*Primary Examiner* — Fabio S Lima
(74) *Attorney, Agent, or Firm* — Oblon, McClelland, Maier & Neustadt, L.L.P.

(57) ABSTRACT

An imaging device that includes a housing mounted on the head of a subject, a camera that is held by the housing and captures an image of an eyeball of the subject, communication circuitry that communicates information with an external device, and controller circuitry that synchronizes together the image captured by the camera and an external signal output from the external device and received.

11 Claims, 17 Drawing Sheets

(56) References Cited

FOREIGN PATENT DOCUMENTS

JP             6638325 B2     1/2020
KR    10-2021-0140808 A    11/2021

OTHER PUBLICATIONS

Japanese Notice of Reasons for Refusal issued May 30, 2023 in Japanese Application No. 2021-079599, (with English Machine translation), 7 pages.

\* cited by examiner

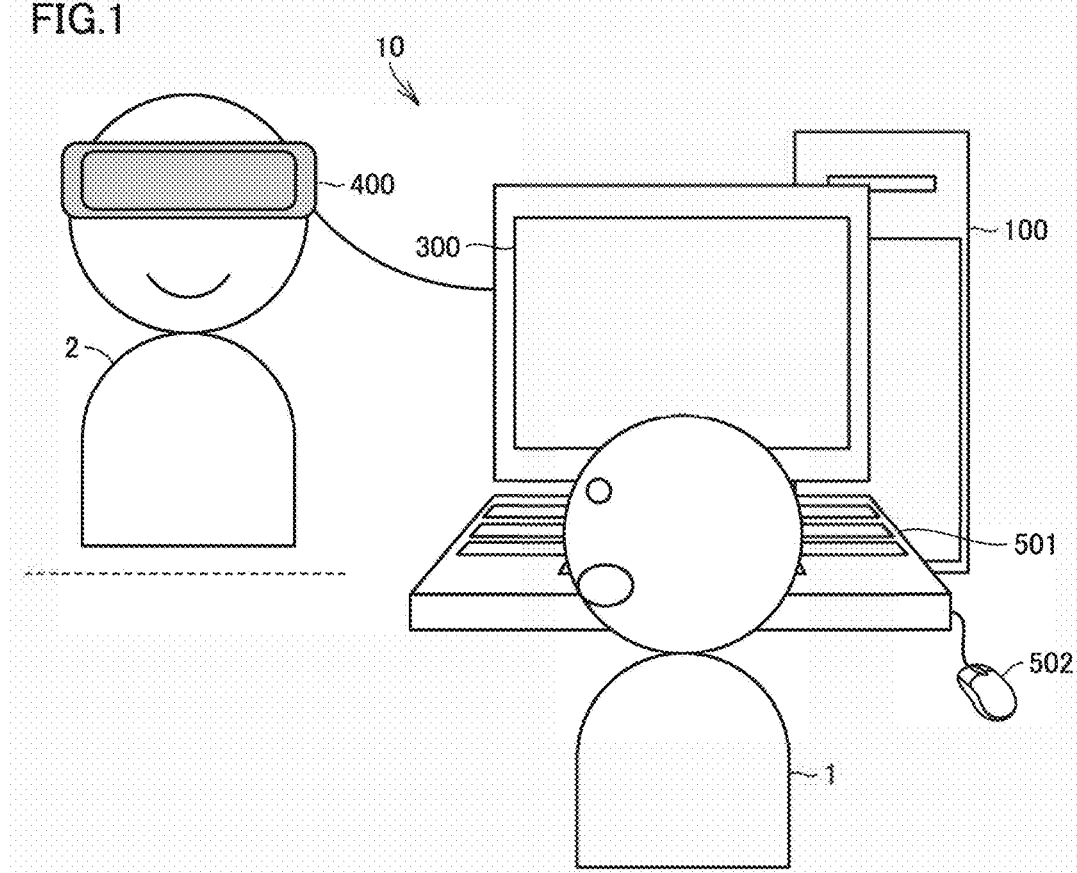

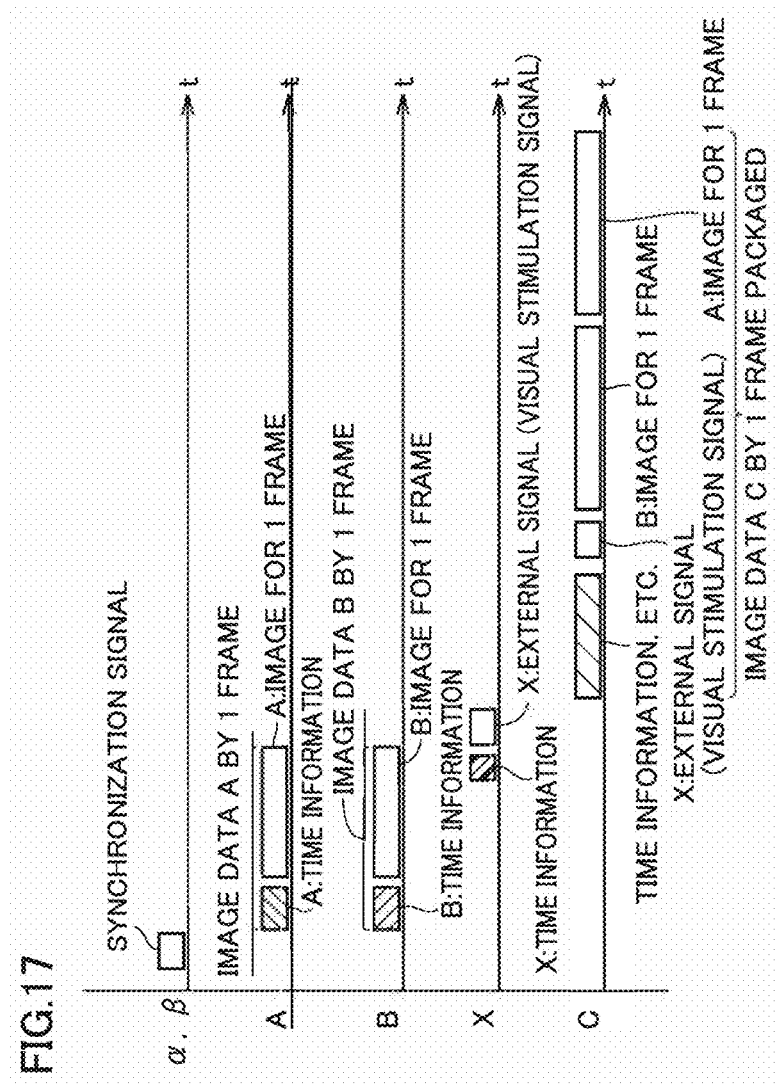

IMAGING DEVICE, OCULAR MOVEMENT DATA PROCESSING SYSTEM, AND CONTROL METHOD

BACKGROUND

Field

The present disclosure relates to an imaging device, an ocular movement data processing system, and a control method.

Description of the Background Art

Conventionally, in making a diagnosis of vertigo, disequilibrium and the like in departments of otorhinolaryngology, neurology, neurosurgery, and the like, equilibrium examinations have been widely carried out to examine how an eyeball moves in response to stimulation of an eye, a head, or an ear. Japanese Patent Laying-Open No. 2014-104120 discloses, as a method used in an equilibrium examination for recording and observing an ocular movement, a method in which an eyeball is imaged by an imaging device and a video thereof is observed and recorded to obtain objective ocular movement image data.

SUMMARY

The ocular movement examination apparatus disclosed in Japanese Patent Laying-Open No. 2014-104120 images ocular movement with an imaging camera. Furthermore, for an ocular movement data processing system which processes, stores and displays image data of an ocular movement to assist a doctor to make a diagnosis, there is a demand for examining the image data of the ocular movement, and together therewith, data of an external device (for example, visual stimulation data and vital signs (a heart rate, a respiration rate, a blood pressure value, a pulse rate, etc.)) to make a more specific diagnosis of vertigo. However, it is cumbersome to timely associate image data of ocular movement with other relevant data.

The present disclosure has been made in order to solve such a problem, and an object of the present disclosure is to provide an imaging device, an ocular movement data processing system, and a control method capable of obtaining image data of ocular movement and relevant data of an external device together therewith.

According to the present disclosure, there is provided an imaging device that captures an image of an eyeball in an equilibrium examination. The imaging device comprises a housing mounted on the head of a subject, an imaging unit that is held by the housing and captures an image of an eyeball of the subject, a communication unit that communicates information with an external device, and a control unit that synchronizes together the image captured by the imaging unit and an external signal output from the external device and received by the communication unit.

According to the present disclosure, there is provided an ocular movement data processing system that processes ocular movement data in an equilibrium examination. The ocular movement data processing system comprises an imaging device that captures an image of an eyeball of a subject, a data processing device that receives data from the imaging device and processes the data, and an external device that obtains at least one of information about the subject and information about an equilibrium examination, wherein the imaging device includes a housing mounted on the head of the subject, an imaging unit that is held by the housing and captures an image of an eyeball of the subject, a communication unit that communicates information with an external device, and a control unit that synchronizes together the image captured by the imaging unit and an external signal output from the external device and received by the communication unit, wherein the communication unit transmits the image and the external signal from the external device that are synchronized together by the control unit to the data processing device, and the data processing device includes a receiving unit that receives from the imaging device the image and the external signal from the external device that are synchronized together, and a processing unit that subjects the image and the external signal from the external device that are synchronized together and received to prescribed data processing.

According to the present disclosure, there is provided a method for control by an imaging device to capture an image of an eyeball in an equilibrium examination, the imaging device including a housing that is mounted on the head of the subject and an imaging unit that is held by the housing and captures an image of an eyeball of the subject. The control method comprises the steps of: causing the imaging unit to capture an image of an eyeball of the subject; receiving an external signal from an external device; and synchronizing together the image captured by the imaging unit and the external signal received from the external device.

The foregoing and other objects, features, aspects and advantages of the present disclosure will become more apparent from the following detailed description of the present disclosure when taken in conjunction with the accompanying drawings.

BRIEF DESCRIPTION OF THE DRAWINGS

FIG. 1 is a schematic diagram showing a configuration of an ocular movement data processing system according to a first embodiment.

FIG. 17 is a schematic diagram for illustrating the first and second imaging units' respective images alternately disposed to output image data.

DETAILED DESCRIPTION OF THE EMBODIMENTS

Figure 2A:
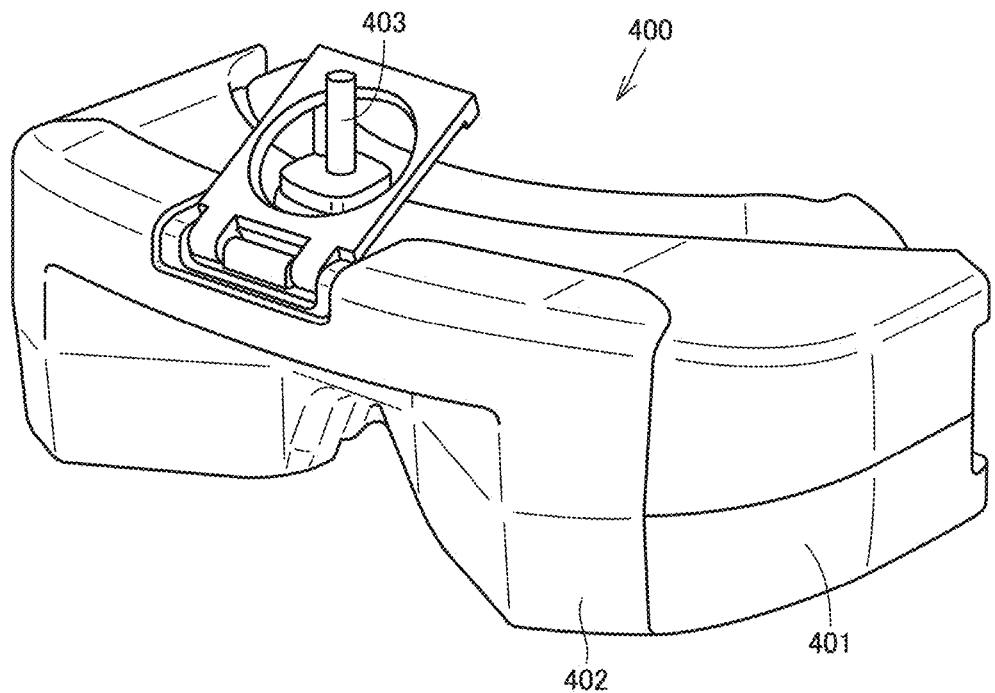
FIG. 2A is a schematic diagram for illustrating a configuration of an imaging device according to the first embodiment.

Embodiments of the present disclosure will be described in detail with reference to the drawings. In the drawings, identical or equivalent components are identically denoted and will not be described redundantly.

First Embodiment

Figure 2B:
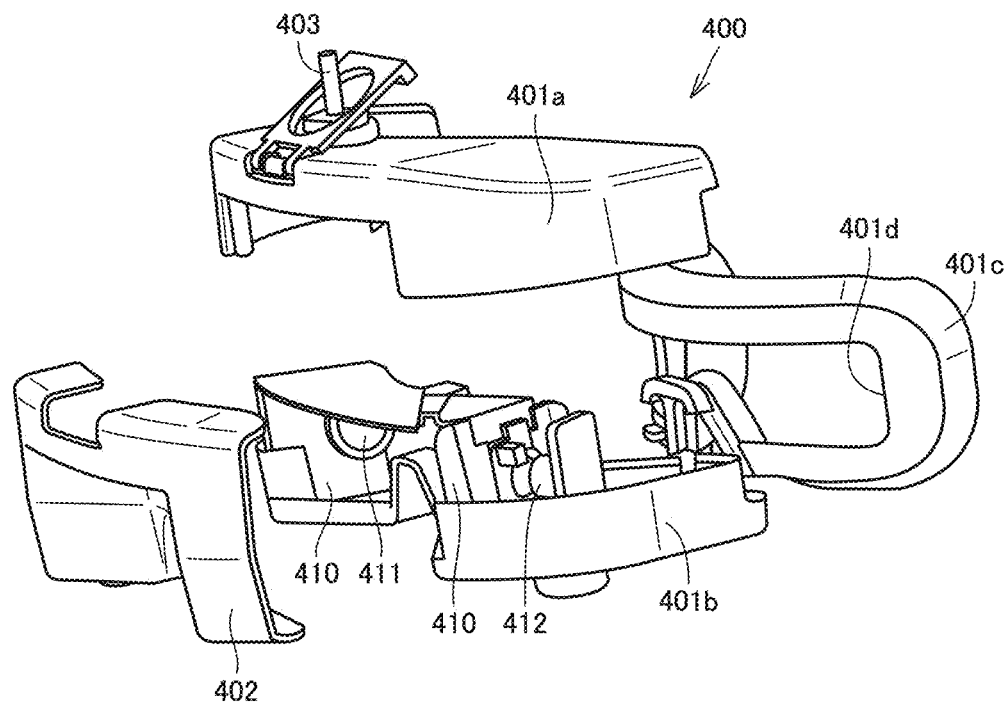
FIG. 2B is a schematic diagram for illustrating the configuration of the imaging device according to the first embodiment.
Figure 3:
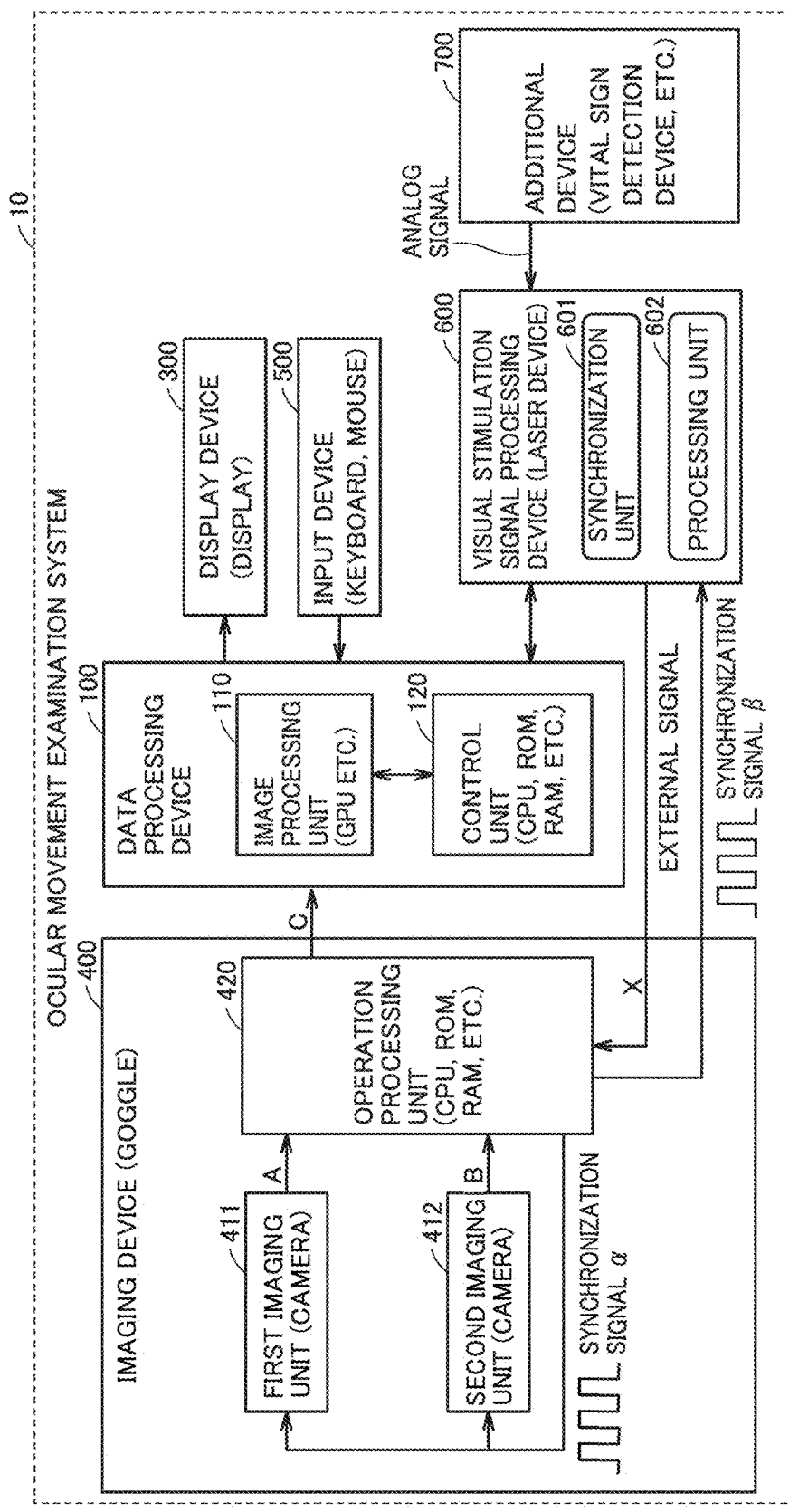
FIG. 3 is a block diagram generally showing a configuration of the ocular movement data processing system according to the first embodiment.

An ocular movement data processing system and an imaging device according to a first embodiment will be described with reference to the drawings. FIG. 1 is a schematic diagram showing a configuration of an ocular movement data processing system 10 according to the first embodiment. FIGS. 2A and 2B are schematic diagrams for illustrating a configuration of an imaging device 400 according to the embodiment. FIG. 3 is a block diagram generally showing a configuration of ocular movement data processing system 10 according to the first embodiment.

An operator 1 can diagnose vertigo of a subject 2 with ocular movement data processing system 10. Note that an "operator" may be any person who uses ocular movement data processing system 10, such as doctors belonging to clinics, general hospitals, university hospitals and the like; teachers, student and the like of medical colleges; and the like. It should be noted that the operator may belong not only to medical departments of ophthalmology, otorhinolaryngology or the like specialized for treatment of vertigo, but also other medical departments such as internal medicine and dentistry. A "subject" may be any person to be diagnosed through ocular movement data processing system 10, such as a patient of a clinic, a general hospital or a university hospital, or a subject in a medical college. "Vertigo" includes a state of subject 2 who suffers some abnormality in his/her vision, such as rotary vertigo causing a vision to spin around, floating dizziness causing a floating sensation, and syncopic dizziness causing a vision to black out.

As shown in FIG. 1, ocular movement data processing system 10 according to the first embodiment comprises a data processing device 100. A display 300, an imaging device 400, a keyboard 501, and a mouse 502 are connected to data processing device 100. Display 300 is an example of a display device. Keyboard 501 and mouse 502 are an example of an input device.

In general, vertigo is diagnosed through observation of nystagmus (an involuntary movement of a rhythmically moving eyeball). Nystagmus includes spontaneous nystagmus that occurs spontaneously with no stimulation applied, and evoked nystagmus caused when stimulation is applied. Further, evoked nystagmus includes positional nystagmus evoked when a head position is displaced, and a positioning nystagmus evoked when a body position is displaced. For evoked nystagmus, it is known that when a physiological rotational stimulus or the like is applied to the head, in particular, the eyeballs move opposite to the head in order to stabilize the field of view, and such a phenomenon is also referred to as vestibulo ocular reflex (VOR).

Specifically, in ocular movement data processing system 10, in order to observe subject 2 for nystagmus, imaging device 400 images the eyeballs of subject 2, and data processing device 100 processes, stores, and displays the image data. Accordingly, data processing device 100 is connected to imaging device 400. Imaging device 400 is a goggle-shaped device mounted on the head of subject 2, and captures an image of the eyeballs of subject 2 and obtains image data of an ocular movement for use in diagnosis of vertigo. As shown in FIG. 1, while subject 2 has imaging device 400 mounted on his/her head, operator 1 performs a nystagmus examination and thus obtains image data of ocular movement of subject 2, and inputs the obtained image data to data processing device 100. Data processing device 100 processes the image data obtained by imaging device 400 and provides operator 1 with information necessary for diagnosis of vertigo.

Imaging device 400 shown in FIG. 2A is in a state such that it has a front side with a shading cover 402 attached thereto. A wiring 403 is provided on an upper surface of housing 401 for connection to data processing device 100. Note that imaging device 400 may be connected to data processing device 100 not only via a wire but also wirelessly insofar as a sufficient transmission rate is ensured for transmission of image data.

Imaging device 400 shown in FIG. 2B is shown disassembled into an upper housing 401a, a lower housing 401b, and an eyepiece 401c brought into contact with subject 2. Lower housing 401b is provided with a first imaging unit 411 that is an infrared imaging device that captures an image of the right eye of subject 2, and a second imaging unit 412 that is an infrared imaging device that captures an image of the left eye of subject 2. Although not shown, upper housing 401a is provided with an operation processing unit 420 shown in FIG. 3. While in the present disclosure a configuration in which first imaging unit 411 and second imaging unit 412 are provided for imaging device 400 will be described, the imaging device may be provided with a single imaging unit and the single imaging unit may be used to capture an image of one or both eyes.

Eyepiece 401c has an opening 401d such that first and second imaging units 411 and 412 can image the eyeballs of subject 2 while subject 2 is covered in front of his/her eyes. Eyepiece 401c is formed of synthetic resin or soft rubber having appropriate flexibility and elasticity so as to be in close contact with the face of subject 2 when the imaging device is mounted on the head of subject 2.

Shading cover 402 is provided with a magnet, for example, and easily detachably attachable to imaging device 400. When shading cover 402 is detached from imaging device 400, subject 2 can see ahead through a hot mirror 410 and thus see an index or the like emitted from a visual stimulation signal processing device 600. Hot mirror 410 is an optical component that is a glass or resin plate coated with a material which transmits visible light and reflects infrared light to obtain an infrared image of an eyeball of the subject while ensuring a field of view for the subject. First and second imaging units 411 and 412 capture an image of the eyeballs of subject 2 reflected by hot mirror 410.

In imaging device 400, as shown in FIG. 3, image data A from first imaging unit 411 and image data B from second imaging unit 412 are processed by operation processing unit 420 and transmitted to data processing device 100 as image data C. First imaging unit 411 includes an infrared imaging device, and a processing circuit (not shown) that attaches information of a frame number and a time stamp (first information) to an image that is captured by the infrared imaging device for each frame to provide image data A and output image data A to operation processing unit 420. The information included in the first information is not limited to a frame number and a time stamp, and may be information of at least one of the frame number and the time stamp, and may include information such as a frame rate, an amount of exposure, and a contrast. Similarly, second imaging unit 412 includes an infrared imaging device, and a processing circuit (not shown) that attaches information of a frame number and a time stamp (second information) to an image that is captured by the infrared imaging device for each frame to provide image data B and output image data B to operation processing unit 420. The information included in the second information is not limited to a frame number and a time stamp, and may be information of at least one of the frame number and the time stamp, and may include information such as a frame rate, an amount of exposure, and a contrast. The first information and the second information are also referred to as information provided for a captured image.

First and second imaging units 411 and 412 can capture an image at 60 frames/sec or 240 frames/sec. The infrared imaging device used for first and second imaging units 411 and 412 is, for example, a CMOS (Complementary Metal Oxide Semiconductor) sensor, a CCD (Charge Coupled Device), or the like capable of capturing an infrared ray.

Operation processing unit 420 performs operation-processing, that is, generates image data C by synchronizing together an image captured by first imaging unit 411 (a first image), an image captured by second imaging unit 412 (a second image) and information of visual stimulation signal processing device 600 and additional device 700. In the present disclosure, visual stimulation signal processing device 600 and additional device 700 may collectively be referred to as an external device. Accordingly, operation processing unit 420 is a computing entity that performs processing of image data, and it is an example of a computer and for example is composed of a central processing unit (CPU), an field-programmable gate array (FPGA), or the like. Furthermore, operation processing unit 420 includes memories such as a random access memory (RAM) for storing images and the like and a read only memory (ROM) for storing programs and the like. In addition to the configuration in which operation processing unit 420 is executed as a control unit (a controller) that synchronizes together the image captured by first imaging unit 411, the image captured by second imaging unit 412, and an external signal received from the external device, operation processing unit 420 also has a configuration in which operation processing unit 420 is executed as a communication unit (a communication circuit) that externally transmits the synchronized images. The external signal from the external device includes a vital signal from a vital sign detection device, a visual stimulation signal from the visual stimulation signal processing device, and the like.

Operation processing unit 420 may use a synchronization signal as a method for synchronizing together the image captured by first imaging unit 411, the image captured by second imaging unit 412, and the external signal received from the external device. Specifically, operation processing unit 420 transmits a synchronization signal $\alpha$ to each of first and second imaging units 411 and 412. First and second imaging units 411 and 412 can use synchronization signal $\alpha$ as a start signal to start an operation (exposure→obtaining a signal→transmission) to obtain their respectively captured first and second images in synchronization. When first and second imaging units 411 and 412 are configured to have no memory for storing two or more pieces of image data, and one imaging unit fails to obtain a signal, operation processing unit 420 can only obtain one piece of image data, and will thus never obtain unsynchronized image data. Operation processing unit 420 transmits a synchronization signal $\beta$ to visual stimulation signal processing device 600. Synchronization signal $\alpha$ and synchronization signal $\beta$ are set to be of the same timing, and operation processing unit 420 synchronizes in accordance with synchronization signal $\beta$ the external signal from the external device with the first and second images synchronized by synchronization signal $\alpha$. Additional device 700 may be directly connected to operation processing unit 420 and operation processing unit 420 may transmit synchronization signal $\beta$ to additional device 700.

When first and second imaging units 411 and 412 and visual stimulation signal processing device 600 have a configuration to provide images and information, respectively, with a time stamp, then, there is a method for synchronization based on the time stamp added to the images and information. The time stamp is generated based on a time counted by a counter of each of first imaging unit 411, second imaging unit 412, and visual stimulation signal processing device 600, and in order to use the time stamp to synchronize images and information, it is necessary to synchronize the time counted by each counter. Accordingly, operation processing unit 420 transmits synchronization signal $\alpha$ to each of first and second imaging units 411 and 412 and transmits synchronization signal $\beta$ to visual stimulation signal processing device 600, and, based on synchronization signals $\alpha$ and $\beta$, first and second imaging units 411 and 412 and visual stimulation signal processing device 600 synchronize and thus adjust times counted by the counters and add a time stamp to their images and information. By synchronizing the image captured by first imaging unit 411, the image captured by second imaging unit 412, and the external signal received from the external device together based on time stamps adjusted by synchronization signals $\alpha$ and $\beta$, operation processing unit 420 can reliably obtain a right eye image and a left eye image of the same timing and can also refer to information of visual stimulation signal processing device 600 and that of additional device 700 of the same timing together. In particular, when first and second imaging units 411 and 412 capture images at 240 frames/sec, simply correlating the images output from the respective imaging units with each other does not provide a right eye image and a left eye image of the same timing and appropriate diagnosis cannot be performed.

Visual stimulation signal processing device 600 is a laser device as shown in FIG. 3, and generates a laser point on a screen and thus displays the laser point as a visual target. Visual stimulation signal processing device 600 can transmit and receive data to and from data processing device 100, and also receives a synchronization signal β from imaging device 400. Visual stimulation signal processing device 600 includes a synchronization unit 601 and a processing unit 602. Based on synchronization signal β received from imaging device 400, synchronization unit 601 synchronizes and adjusts time counted by a counter and provides a time stamp to processing unit 602.

Furthermore, visual stimulation signal processing device 600 is connectable to an additional device 700 such as a vital sign detection device. Visual stimulation signal processing device 600 receives an analog signal of a vital sign (a heart rate, a respiration rate, a blood pressure value, a pulse rate, etc.) from additional device 700, and converts the analog signal into a vital signal of a digital signal by processing unit 602. Visual stimulation signal processing device 600 includes the vital signal in an external signal of visual stimulation signal processing device 600, adds a time stamp of synchronization unit 601 to the external signal, and outputs the external signal with the time stamp to imaging device 400. The external signal output from the external device includes information of the external device, such as a vital signal of additional device 700 and the visual stimulation signal of visual stimulation signal processing device 600. Operation processing unit 420 can use time stamps to synchronize the image captured by first imaging unit 411, the image captured by second imaging unit 412, and the external signal received from the external device together. Note that the visual stimulation signal specifically includes a signal indicating that a visual target is projected on the screen and visual stimulation is thus generated, a positional signal (a signal of XY coordinates) of an index on the screen serving as visual stimulation, and the like.

Synchronization signals α and β transmitted by operation processing unit 420 to first and second imaging units 411 and 412 and visual stimulation signal processing device 600, respectively, are clock signals repeated periodically as prescribed (for example at 60 Hz). This is not exclusive, however, and operation processing unit 420 may transmit a single-shot pulse signal as synchronization signals α and β to first and second imaging units 411 and 412 and visual stimulation signal processing device 600, respectively, as timed when started, as prescribed, or the like.

Further, operation processing unit 420 may not transmit synchronization signals α and β to first and second imaging units 411 and 412 and visual stimulation signal processing device 600, respectively, and may instead synchronize the time counted by each counter, for example as timed when first and second imaging units 411 and 412 and visual stimulation signal processing device 600 are powered on. Further, operation processing unit 420 may not provide synchronization based on a time stamp added to each image and information, and when first and second imaging units 411 and 412 have a configuration to each provide an image with a frame number and visual stimulation signal processing device 600 has a configuration to provide information with a number, operation processing unit 420 may provide synchronization based on the frame number added to the image and the number added to the information.

Figure 4:
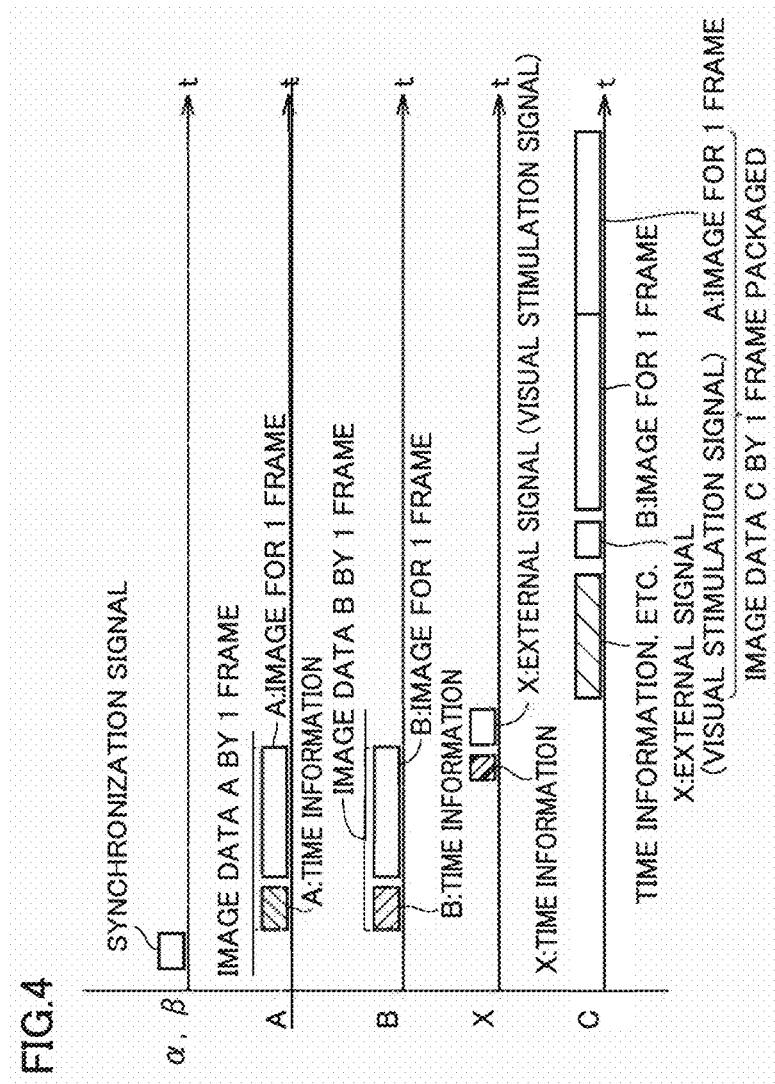
FIG. 4 is a schematic diagram representing image data of each of a first imaging unit and a second imaging unit, data of a visual stimulation signal processing device, and image data output by an operation processing unit.

FIG. 4 is a schematic diagram representing image data of each of first imaging unit 411 and second imaging unit 412, data of visual stimulation signal processing device 600, and image data output by operation processing unit 420. As shown in FIG. 4, first imaging unit 411 adds time information (a frame number, a time stamp, etc.) to an image of one frame and outputs the image with the time information as image data A. Similarly, as shown in FIG. 4, second imaging unit 412 adds time information (a frame number, a time stamp, etc.) to an image of one frame and outputs the image with the time information as image data B. Visual stimulation signal processing device 600 adds time information (a number, a time stamp, etc.) to the visual stimulation signal and outputs the visual stimulation signal with the time information as data X. As shown in FIG. 4, operation processing unit 420 processes the image of one frame of first imaging unit 411 and the image of one frame of second imaging unit 412 including the same time information as one image, and outputs the processed image, data X of visual stimulation signal processing device 600 and the time information as one image data C. Image data C provides both eyes' real-time images as one image data, and is thus suitable for simultaneously displaying both eyes' images in data processing device 100 without delay. Image data C shown in FIG. 4 has the time information of data X, the time information of image data A, and the time information of image data B combined into one piece of time information, followed by the visual stimulation signal of data X, and the image of one frame of image data A and the image of one frame of image data B that are processed into one image. This is not exclusive, however, and image data C may not have the time information of data X combined with those of image data A and B, and may instead have data X simply aligned with the processed one image.

Figure 5:
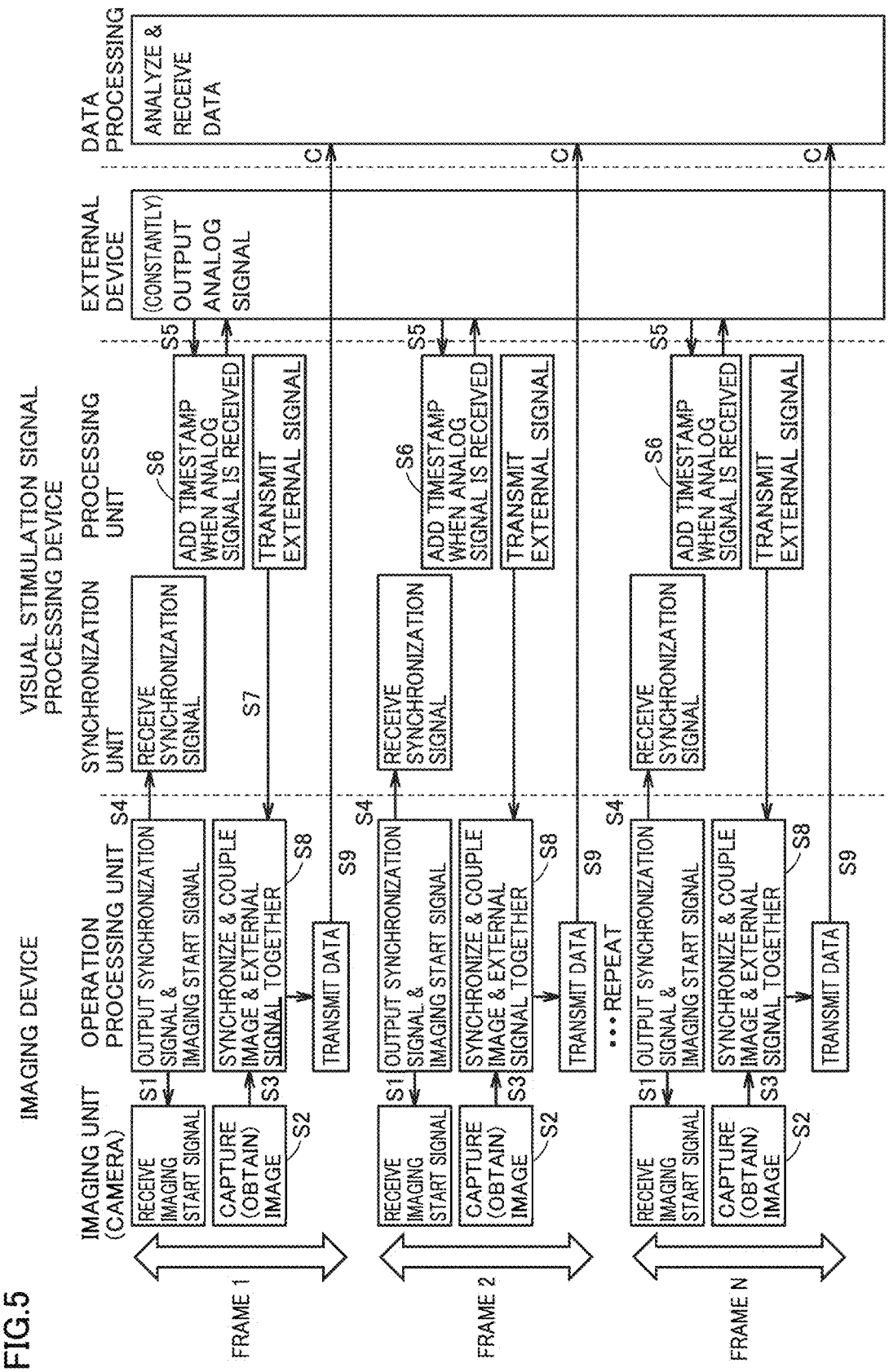
FIG. 5 is a sequence diagram for illustrating transmission and reception of data among the imaging device, the visual stimulation signal processing device, and an external device.

Transmission and reception of information including additional device 700 will be described. FIG. 5 is a sequence diagram for illustrating transmission and reception of data among the imaging device, the visual stimulation signal processing device, and the external device. Initially, operation processing unit 420 outputs a synchronization signal α and a start imaging signal to the imaging unit (first imaging unit 411 and second imaging unit 412) (S1). Operation processing unit 420 outputs synchronization signal β to synchronization unit 601 of visual stimulation signal processing device 600. When the imaging unit (first imaging unit 411 and second imaging unit 412) receives the start imaging signal, the imaging unit starts capturing an image of an eye, based on a predetermined setting, to obtain an image of an eyeball (S2). The imaging unit (first imaging unit 411 and second imaging unit 412) adds to the obtained image a time stamp synchronized based on synchronization signal α and outputs the image with the time stamp as image data A and B to operation processing unit 420 (S3).

Operation processing unit 420 outputs synchronization signal β to synchronization unit 601 of visual stimulation signal processing device 600 (S4). Synchronization unit 601 provides adjustment to synchronize a counter based on synchronization signal β received. Additional device 700 outputs an analog signal such as a vital sign to visual stimulation signal processing device 600 (S5). Processing unit 602 of visual stimulation signal processing device 600 converts the received analog signal into a digital signal to provide an external signal and adds a time stamp of synchronization unit 601 to the external signal (S6). Processing unit 602 transmits to operation processing unit 420 the external signal received from the external device (S7). The external signal from the external device may include information such as the visual stimulation signal of visual stimulation signal processing device 600 in addition to the vital signal of additional device 700.

Operation processing unit 420 synchronizes the images of first and second imaging units 411 and 412 and the external signal from the external device together based on the time stamps added to the images and the external signal. Operation processing unit 420 combines the image of first imaging unit 411 and the image of second imaging unit 412 together, and further combines the external signal from the external device thereto to generate image data C (S8).

Subsequently operation processing unit 420 transmits the generated image data C to data processing device 100 (S9). Data processing device 100 processes the received image data C, and processes, stores, and displays captured image data.

The above process is performed for one frame, and the same process is repeated for each frame. FIG. 5 illustrates processing frames 1, 2, . . . , and N.

Figure 6:
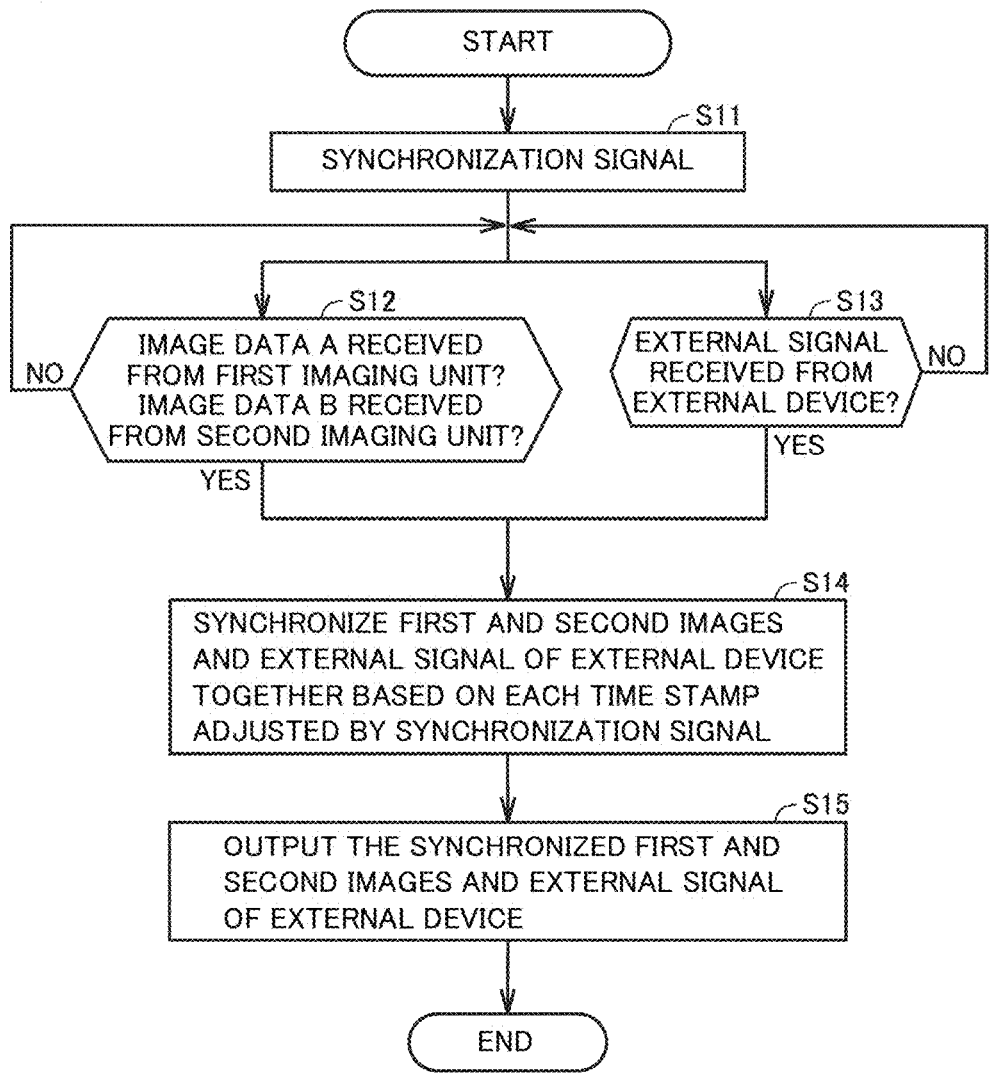
FIG. 6 is a flowchart of a method for controlling the imaging device according to the first embodiment.

Hereinafter reference will be made to a flowchart to describe a control method in which imaging device 400 synchronizes an image captured by first imaging unit 411, an image captured by second imaging unit 412, and the external signal from the external device together to output an image, information and the like. FIG. 6 is a flowchart of a method for controlling imaging device 400 according to the first embodiment. Initially, operation processing unit 420 transmits synchronization signals α and β to first and second imaging units 411 and 412 and visual stimulation signal processing device 600 (step S11). First and second imaging units 411 and 412 and visual stimulation signal processing device 600 perform adjustment based on synchronization signals α and β to synchronize times counted by their respective counters.

Operation processing unit 420 determines whether image data A (first image data) is received from first imaging unit 411 and image data B (second image data) is received from second imaging unit 412 (step S12). When image data A and B are not received (NO in step S12), operation processing unit 420 returns to step S12. When image data A and B are received (YES in step S12), operation processing unit 420 proceeds to step S14. Operation processing unit 420 determines whether an external signal (information such as a visual stimulation signal and a vital sign) from an external device has been received from visual stimulation signal processing device 600 (step S13). When there is no external signal received from an external device (NO in step S13), operation processing unit 420 returns to step S13. While in the flowchart shown in FIG. 6, image data A, image data B, and the external signal from the external device are input to operation processing unit 420 at the same time, image data A from first imaging unit 411, image data B from second imaging unit 412, and the external signal from the external device from visual stimulation signal processing device 600 may be input to operation processing unit 420 sequentially.

When there is an external signal received from an external device (YES in step S13), operation processing unit 420 synchronizes the image captured by first imaging unit 411 (a first image), the image captured by second imaging unit 412 (a second image) and the external signal from the external device together based on time stamps adjusted by synchronization signals α and β (step S14). When information of any one of image data A and B from the first and second imaging units in step S12 and the external signal from the external device in step S13 is not received and another information is received, the received one(s) of information of image data A and B and the external signal may alone be synchronized with the received other information. When one of information is not received, then the synchronization step of step 14 may not be performed and the control may return to step S12 and step S13. Operation processing unit 420 outputs the image captured by first imaging unit 411 (the first image) and the image captured by second imaging unit 412 (the second image) as well as the external signal from the external device that are synchronized together (step S15).

Figure 7:
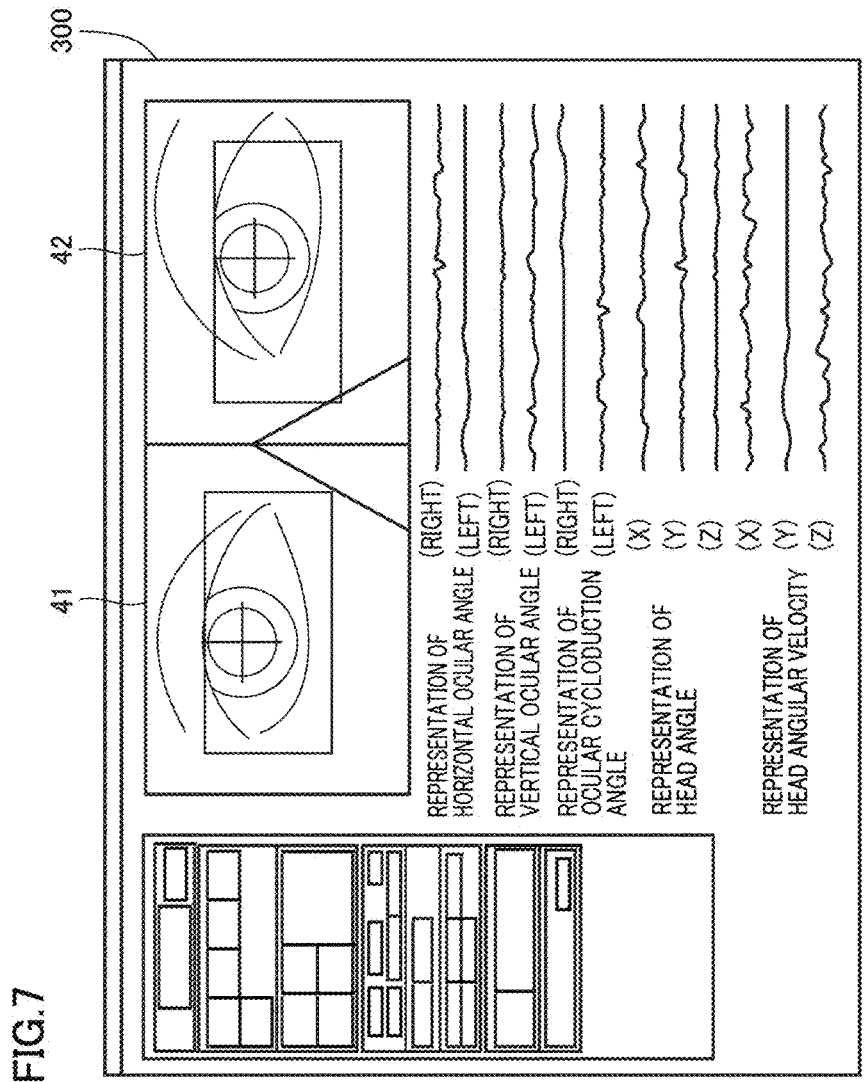
FIG. 7 is a schematic diagram showing an example of an image of the eyeballs of a subject and data of an ocular movement thereof displayed on a display of a data processing device.

Subsequently, the image captured by first imaging unit 411 (the first image) and the image captured by second imaging unit 412 (the second image) as well as the external signal from the external device that are synchronized together are transmitted to data processing device 100, and processing of ocular movement data required for diagnosis of vertigo is performed. FIG. 7 is a schematic diagram showing an example of an image of the eyeballs of subject 2 and data of an ocular movement thereof displayed on display 300 of data processing device 100. The example of displaying by display 300 shown in FIG. 7 displays on a screen at an upper side a first image 41 captured by first imaging unit 411 and a second image 42 captured by second imaging unit 412. Data processing device 100 can sample first image 41 and second image 42 for each frame, binarize the sampled images to perform elliptical approximation, or apply a template image to the sampled images to perform pattern-matching to detect each eyeball's pupil contour and center. An image indicating each eyeball's pupil contour and center, as detected by data processing device 100, is superimposed and displayed on first image 41 and second image 42 displayed on display 300.

As shown in FIG. 3, data processing device 100 includes an image processing unit 110 and a control unit 120. Image processing unit 110 is composed of a graphics processing unit (GPU) or the like, and can cause display 300 to display first image 41 and second image 42, and superimpose an image indicating each eyeball's pupil contour and center on first image 41 and second image 42 and thus display the superimposed images on display 300. Control unit 120 is a computing entity which performs elliptical approximation or uses a template image to perform pattern-matching or the like to detect an eyeball's pupil contour and center. It is an example of a computer composed for example of a CPU, an FPGA, or the like. Further, control unit 120 includes memory such as a RAM used to store an image or the like and a ROM having a program or the like stored therein. In addition to the configuration in which control unit 120 is executed as a processing unit (a processor) that subjects the synchronized first and second images 41 and 42 to prescribed data processing, control unit 120 also has a configuration in which control unit 120 is executed as a receiving unit (a receiving circuit) that receives the synchronized first and second images 41 and 42 from imaging device 400.

Control unit 120 further determines a horizontal ocular angle (right), a vertical ocular angle (right) and an ocular cycloduction angle (right) from first image 41, and a horizontal ocular angle (left), a vertical ocular angle (left) and an ocular cycloduction angle (left) from second image 42, each through an operation. Specifically, control unit 120 determines each eyeball's pupil contour and center position of first image 41 and second image 42 as detected for each frame, and from the position calculates horizontal ocular angles (right and left), vertical ocular angles (right and left), and ocular cycloduction angles (right and left). Data processing device 100 records how the horizontal ocular angles (right and left), vertical ocular angles (right and left), and ocular cycloduction angles (right and left) calculated by control unit 120 change in value with time, and causes display 300 to display it on a screen at a lower side.

Although not shown, imaging device 400 is provided with a head sensor including an acceleration sensor and an angular velocity sensor, and the head sensor outputs a measurement signal corresponding to the movement of the head of subject 2. The head sensor may be mounted on the head of subject 2 separately from imaging device 400. Operation processing unit 420 or control unit 120 determines a head angle and a head angular velocity through an operation based on the measurement signal received from the head sensor. Data processing device 100 records how the head angle and head angular velocity calculated by operation processing unit 420 or control unit 120 change in value with time, and causes display 300 to display it on the screen at a lower side. Head angle and head angular velocity are represented in a graph, which represent them in value along each of three axes (X-, Y- and Z-axes).

Figure 8:
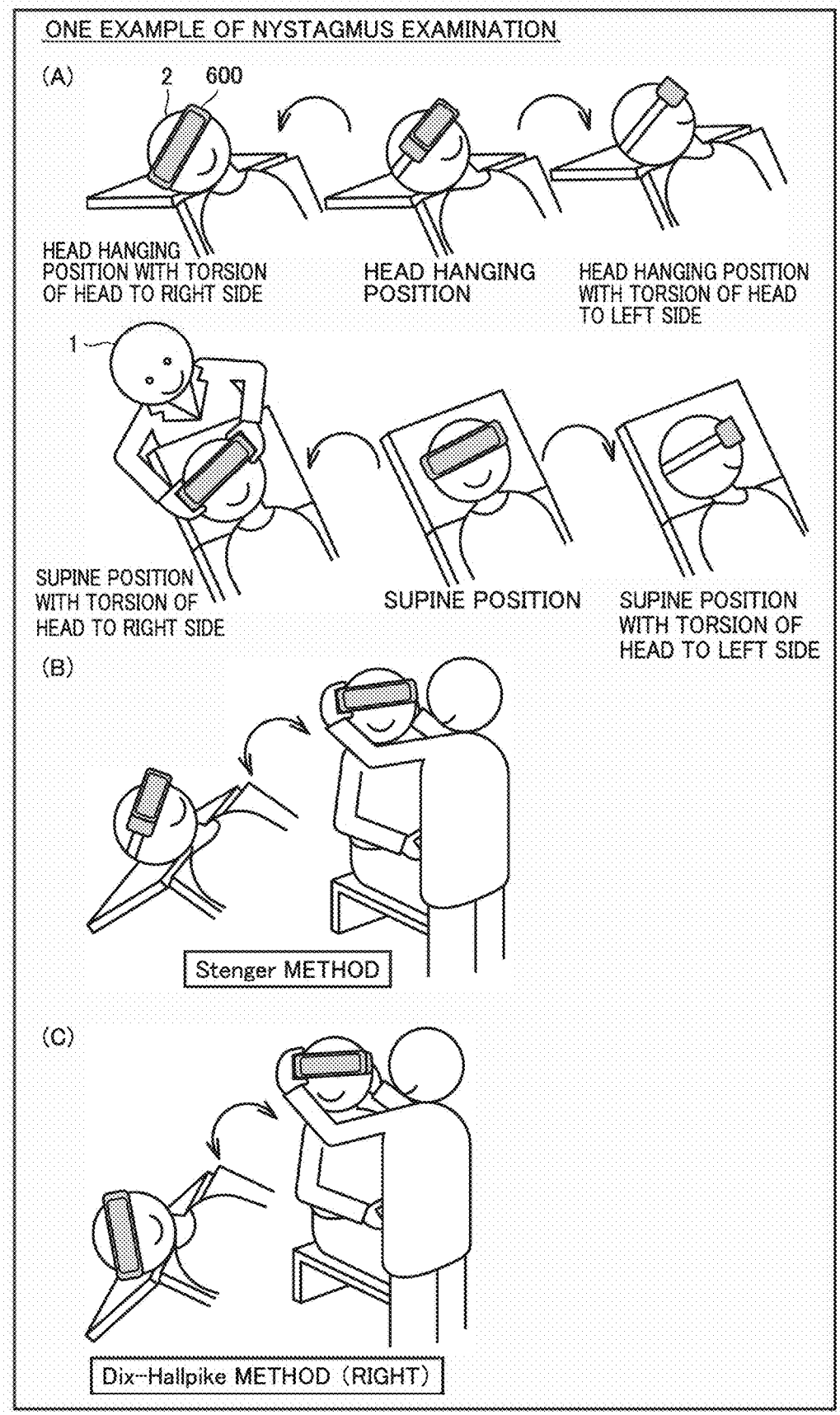
FIG. 8 is a schematic diagram for illustrating an example of a nystagmus examination.

Further, an example of a nystagmus examination used in diagnosis of vertigo will be described. FIG. 8 is a schematic diagram for illustrating an example of a nystagmus examination. The nystagmus examination is performed under a prescribed condition. For example, in an examination for spontaneous nystagmus, operator 1 diagnoses vertigo based on an ocular movement of subject 2 while the subject has his/her head fixed and thus gazes frontward. In an examination for positional nystagmus, as shown in FIG. 8A, operator 1 diagnoses vertigo based on an ocular movement of subject 2 induced as the subject displaces his/her head's position to various positions. In an examination for positioning nystagmus, as shown in FIGS. 8(B) and 8(c), operator 1 diagnoses vertigo based on an ocular movement of subject 2 induced as the operator 1 displaces the subject's bodily and head positions.

Figure 9:
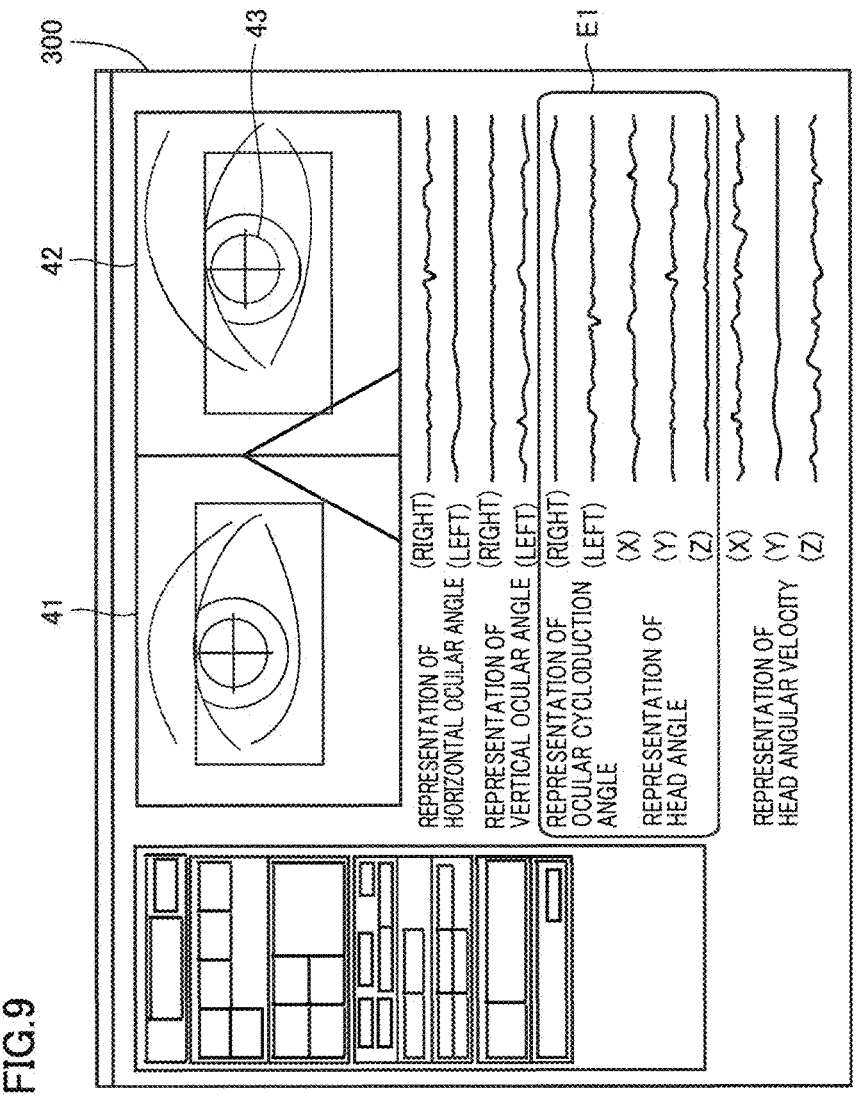
FIG. 9 is a schematic diagram showing an example of an image of the eyeballs of a subject and data of an ocular movement thereof displayed on a display in a nystagmus examination.

FIG. 9 is a schematic diagram showing an example of an image of the eyeballs of subject 2 and data of an ocular movement thereof displayed on a display in a nystagmus examination. Data processing device 100 in the nystagmus examination processes ocular movement data from an image of the pupil, iris pattern and the like of an eyeball of subject 2. When subject 2 has only a single eye imaged with an imaging device during a nystagmus examination, and the subject assumes some head position, the subject may lower one eyelid or the like, and the imaging device may be unable to constantly obtain an image of the eyeball. In contrast, imaging device 400 obtains images of both eyes of subject 2 through first and second imaging units 411 and 412, respectively, and synchronizes the images and thus processes data, and even if the subject lowers one eyelid or the like and one eyeball's image cannot be obtained, the other eyeball's image of the same timing has been obtained without fail. Thus, even when subject 2 changes his/her head position during a nystagmus examination, data processing device 100 ensures that an image of an eyeball allowing data to be processed is obtained, and data processing device 100 can thus steadily process ocular movement data of subject 2. In the example shown in FIG. 9, the nystagmus examination is performed by processing data E1 of how ocular cycloduction angles (right and left) and a head angle change with time.

Figure 10:
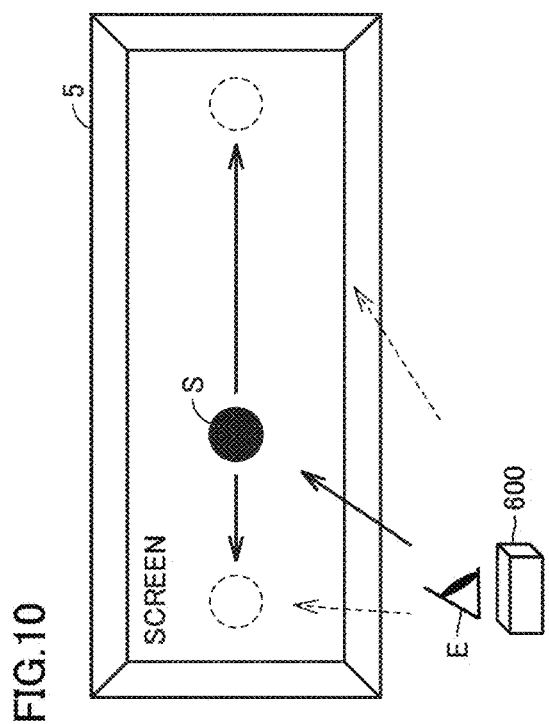
FIG. 10 is a schematic diagram for illustrating an example of a visual stimulation test.

Hereinafter, an example of a visual stimulation test employed in diagnosis of vertigo will be described. FIG. 10 is a schematic diagram for illustrating an example of a visual stimulation test. FIG. 10 shows a screen 5 for projecting a visual target S generated by visual stimulation signal processing device 600, and shows how visual target S is positionally moved rightward/leftward as it is positionally changed by visual stimulation signal processing device 600. Visual target S may positionally not be moved rightward/leftward and instead be moved upward/downward or upward/downward/rightward/leftward. When the visual stimulation test is performed, subject 2 wears imaging device 400 having detached therefrom shading cover 402 shown in FIG. 2A, and subject 2 can thus visually recognize visual target S projected on screen 5 through hot mirror 410.

Visual stimulation signal processing device 600 includes a laser device to generate a laser point on screen 5 shown in FIG. 10 and thus display the laser point as visual target S. As shown in FIG. 3, visual stimulation signal processing device 600 can transmit and receive data to and from data processing device 100, and also receives a synchronization signal β from imaging device 400. Visual stimulation signal processing device 600 adds a time stamp of synchronization unit 601 to the visual stimulation signal and an external signal received from an external device such as a vital sign detection device, and outputs the signal with the time stamp to the imaging device 400.

Figure 11:
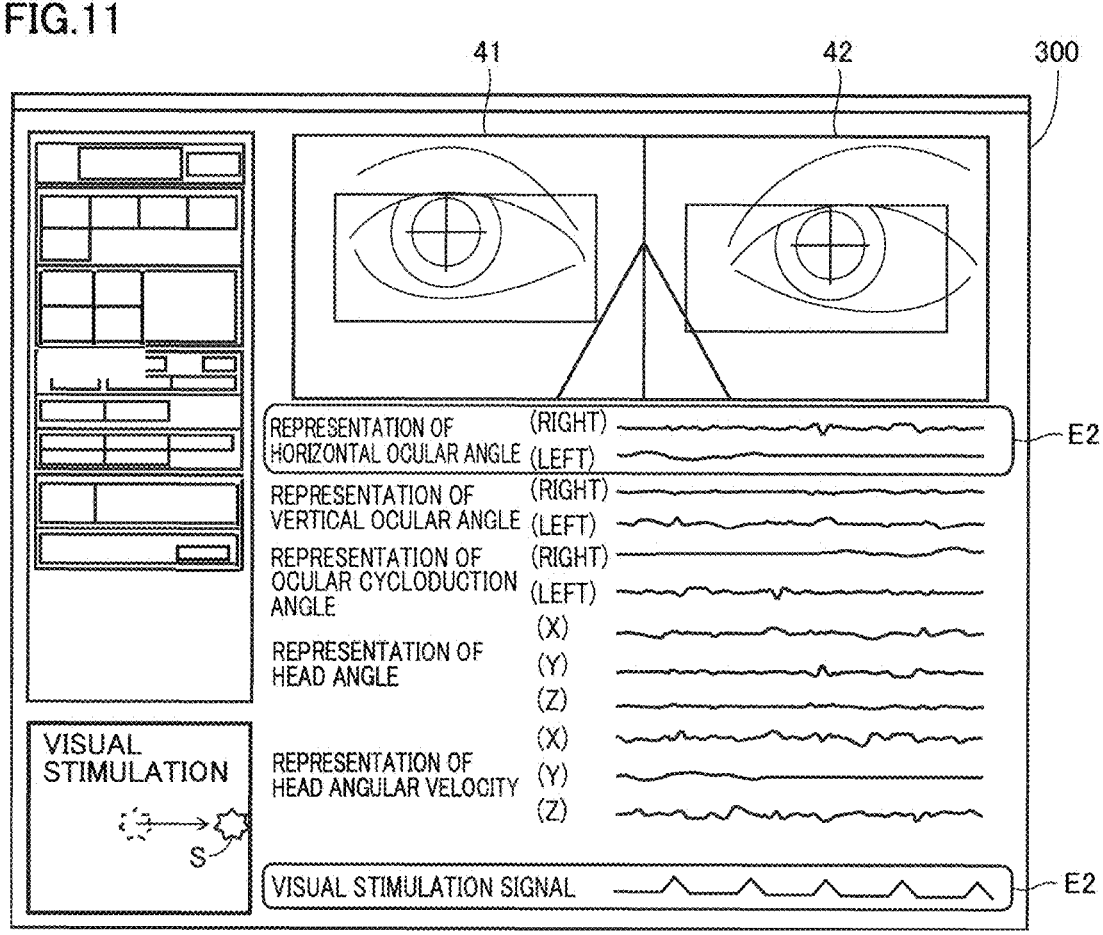
FIG. 11 is a schematic diagram showing an example of an image of the eyeballs of a subject and data of an ocular movement thereof displayed on a display in a visual stimulation test.

FIG. 11 is a schematic diagram showing an example of an image of the eyeballs of subject 2 and data of an ocular movement thereof displayed on a display in a visual stimulation test. Data processing device 100 in the FIG. 10 visual stimulation test processes ocular movement data from an image of the pupil, iris pattern and the like of an eyeball of subject 2. A pursuit eye movement test, which is an example of the visual stimulation test, examines how an eyeball of subject 2 follows visual target S. Accordingly, in the example shown in FIG. 11, data processing device 100 performs the pursuit eye movement test by processing data E2 of how horizontal ocular angles (right and left) and a visual stimulation signal change with time. Note that, in FIG. 11, display 300 displays on a screen at a lower side a graph corresponding to how a visual stimulation signal of those received from visual stimulation signal processing device 600 that indicates that visual stimulation is generated, changes with time. Further, display 300 displays on the screen at a lower left side that visual target S projected on screen 5 positionally moves from left to right, based on a signal of XY coordinates of visual target S included in the visual stimulation signal. When visual target S positionally moves upward/downward rather than rightward/leftward, data E2 needs to be how vertical ocular angles (right and left) and a vertical visual stimulation angle change with time, and when visual target S positionally moves upward/downward/rightward/leftward, data E2 needs to be how horizontal ocular angles (right and left), vertical ocular angles (right and left), a horizontal visual stimulation angle and a vertical visual stimulation angle change with time.

Another example of the visual stimulation test is a saccadic eye movement test. In the saccadic eye movement test, visual target S flashed on/off right and left alternately or the like is shown to subject 2 to test how the eyeballs of subject 2 move. Processing ocular movement data of subject 2 in the saccadic eye movement test requires sampling an image at a rate of 6 ms=166 fps or more. Accordingly, imaging device 400 is required to capture an image of the eyeballs of subject 2 at a high sampling rate of 240 fps rather than doing so at a normal sampling rate of 60 fps.

Figure 12:
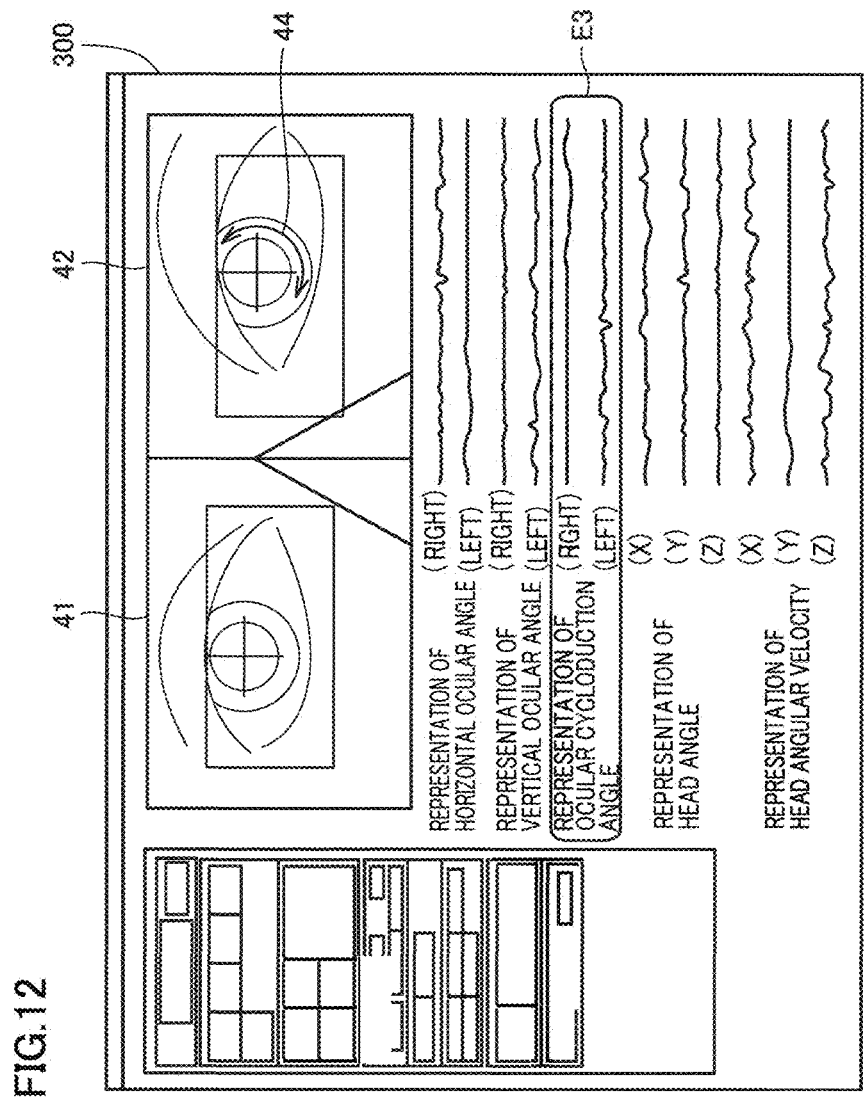
FIG. 12 is a schematic diagram showing an example of an image of the eyeballs of a subject and data of an ocular movement thereof displayed on a display when ocular cycloduction movement data is processed.

In addition, ocular cycloduction movement data may be processed in diagnosis of vertigo. FIG. 12 is a schematic diagram showing an example of an image of the eyeballs of subject 2 and data of an ocular movement thereof displayed on a display when ocular cycloduction movement data is processed. Data processing device 100 processes ocular cycloduction movement data from recognition (or pattern-matching) of an image of the pupil, iris pattern and the like of an eyeball of subject 2. When processing ocular cycloduction movement data, data processing device 100 detects ocular cycloduction movement, as indicated in FIG. 12 by an arrow 44, records how an ocular cycloduction angle changes with time, and causes display 300 to display it on a screen at a lower side. Data processing device 100 processes ocular cycloduction movement data of subject 2 by examining data E3 of how ocular cycloduction angles (right and left) change with time.

Figure 13:
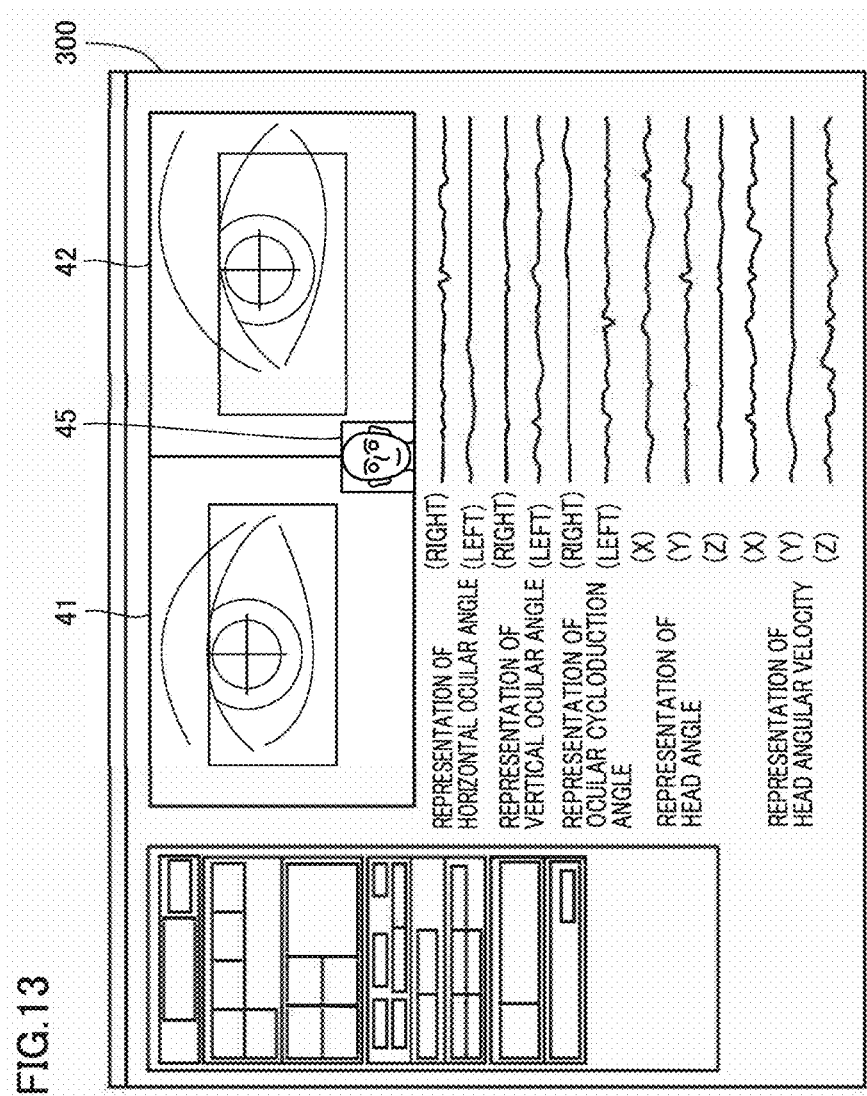
FIG. 13 is a schematic diagram of superimposing an image representing an orientation of the head of a subject on an image of the eyeballs of the subject, and causing a display to display the thus superimposed images.

Further, in diagnosis of vertigo, the orientation of the head is also important information along with ocular movement, and accordingly, operator 1 desires to be able to recognize an image of an eyeball and the orientation of the head simultaneously. Accordingly, data processing device 100 superimposes the image of the eyeball and an image representing the orientation of the head, one on the other, and causes display 300 to display the superimposed images. FIG. 13 is a schematic diagram of superimposing an image representing an orientation of the head of subject 2 on an image of the eyeballs of the subject, and causing a display to display the thus superimposed images. On the screen shown in FIG. 13 at an upper side are displayed first image 41 captured by first imaging unit 411 and second image 42 captured by second imaging unit 412, with an image 45 therebetween indicating the orientation of the head of subject 2. Image 45 indicating the orientation of the head of subject 2 shows in a 3D model of the head the orientation of the head based on information of a head angle and a head angular acceleration as measured by the head sensor. Image 45 indicating the orientation of the head of subject 2 is not limited to the 3D model of the head as shown in FIG. 13, and may for example be displayed in the form of a 2D model, textual information, etc.

Figure 14:
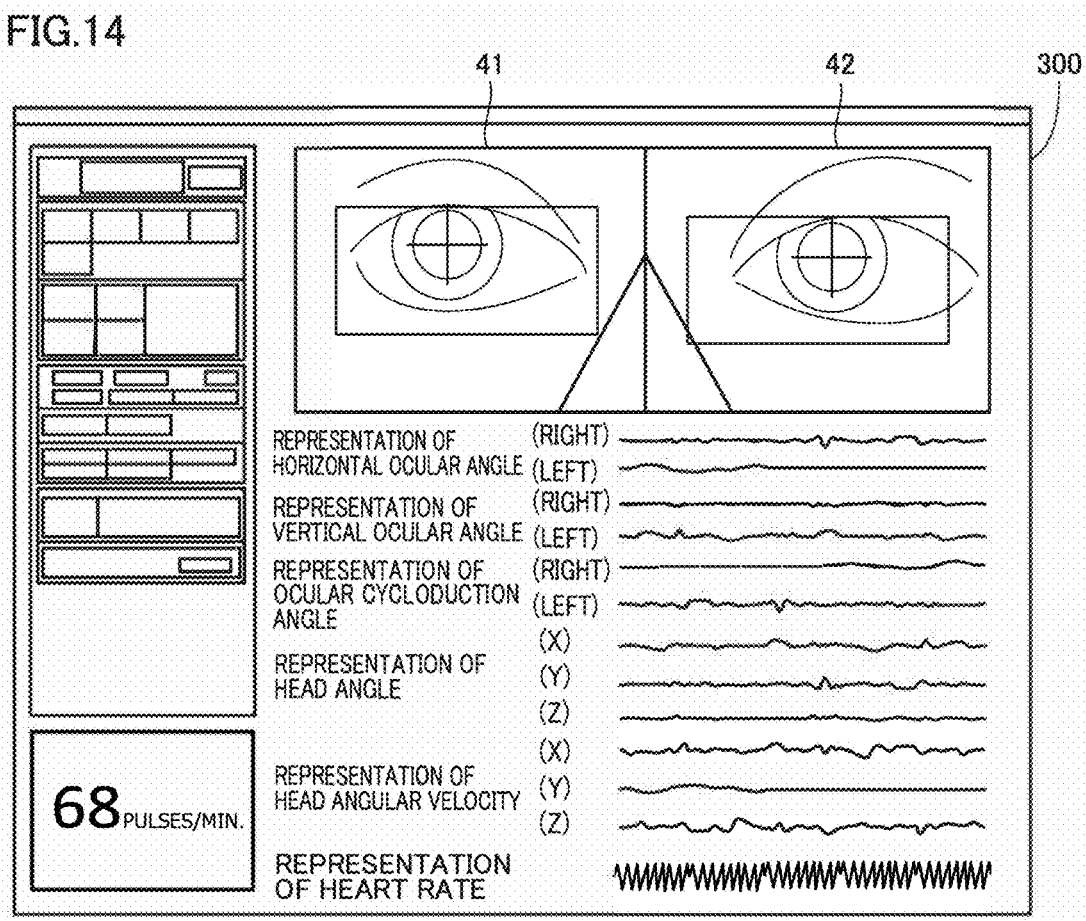
FIG. 14 is a schematic diagram of superimposing an image of the eyeballs of the subject and information of a vital signal, one on the other, and causing a display to display the same.

Further, in diagnosis of vertigo, information of a vital sign (such as a heart rate) is also important information along with ocular movement, and accordingly, operator 1 desires to be able to recognize an image of an eyeball and the information of the vital sign simultaneously. Accordingly, data processing device 100 superimposes the image of the eyeball and an image representing the information of the vital sign, one on the other, and causes display 300 to display the superimposed images. FIG. 14 is a schematic diagram of superimposing an image of the eyeballs of a subject and information of a vital signal, one on the other, and causing a display to display the same. On the screen shown in FIG. 14 at an upper side are displayed first image 41 captured by first imaging unit 411 and second image 42 captured by second imaging unit 412, and at a lower side is displayed a graph corresponding to how a heart rate included in the vital signal received from additional device 700 changes with time. Further, display 300 digitally displays on the screen at a lower left side a heart rate of subject 2 based on the vital signal received from additional device 700.

As described above, imaging device 400 according to the first embodiment is a device that captures an image of an eyeball in an equilibrium examination. Imaging device 400 comprises housing 401 mounted on the head of subject 2, an imaging unit (first imaging unit 411 and second imaging unit 412) that is held by housing 401 and captures an image of an eyeball of subject 2, operation processing unit 420 (a communication unit) that communicates information with an external device (visual stimulation signal processing device 600 and additional device 700), and operation processing unit 420 (a control unit) that synchronizes together the image captured by the imaging unit (first imaging unit 411 and second imaging unit 412) and an external signal received from the external device.

Thus, imaging device 400 according to the first embodiment synchronizes together the image captured by the imaging unit (first imaging unit 411 and second image unit 412) and the external signal received from the external device, and can thus obtain image data of ocular movement, and together therewith, relevant data of the external device.

Operation processing unit 420 transmits the image and the external signal from the external device that are synchronized together to data processing device 100 that is externally provided and processes data. Data processing device 100 can thus process data of the image and the external signal from the external device that are synchronized together, and an appropriate diagnosis of vertigo can thus be made.

The imaging unit (first imaging unit 411 and second imaging unit 412) adds information provided for each captured image (the first information and the second information) to the captured image to provide image data A and B and outputs image data A and B to operation processing unit 420, operation processing unit 420 synchronizes together image data A and B output by the imaging unit (first imaging unit 411 and second imaging unit 412) and the external signal received from the external device, and transmits the same to data processing device 100 as image data A and B including the information provided for the captured image (the first information and the second information) and the external signal from the external device. Thus, operation processing unit 420 can reliably synchronize first and second images 41 and 42 and the external signal from the external device together based on the information provided for captured images (the first information and the second information) included in image data A and B.

Operation processing unit 420 transmits synchronization signals α and β to the imaging unit (first imaging unit 411 and second imaging unit 412) and visual stimulation signal processing device 600, and the imaging unit (first imaging unit 411 and second imaging unit 412) and visual stimulation signal processing device 600 synchronize the information provided for captured images (the first information and the second information) and added thereto and information of visual stimulation signal processing device 600 together based on synchronization signals α and β. Operation processing unit 420 can thus reliably perform adjustment of synchronizing the first information of first imaging unit 411, the second information of second imaging unit 412 and the information of visual stimulation signal processing device 600 together. Synchronization signals α and β transmitted to the imaging unit (first and second imaging units 411 and 412) and visual stimulation signal processing device 600 are signals repeated periodically as prescribed.

The information provided for captured images (the first information and the second information) and the external signal from the external device at least include information of a time stamp. Operation processing unit 420 can reliably synchronize first image 41, second image 42, and the external signal from the external device together based on a time stamp included in image data A and B and a time stamp included in the external signal from the external device.

The imaging unit includes first imaging unit 411 that captures an image of one eyeball of subject 2 and second imaging unit 412 that is held in housing 401 and captures an image of the other eyeball of subject 2, and first imaging unit 411 outputs each captured first image 41 with first information added thereto as image data A to operation processing unit 420 and second imaging unit 412 outputs each captured second image 42 with second information added thereto as image data B to operation processing unit 420, and operation processing unit 420 synchronizes first image 41, second image 42, and the external signal from the external device together based on the first information included in image data A, the second information included in image data B, and the external signal from the external device and externally transmits image data A and B and the external signal from the external device that are synchronized together. Thus, operation processing unit 420 can reliably synchronize first image 41, second image 42, and the external signal from the external device together based on the first information included in image data A, the second information included in image data B, and the external signal from the external device.

Operation processing unit 420 processes the synchronized first and second images 41 and 42 as one image, and operation processing unit 420 externally transmits image data C including the processed image, the external signal (a visual stimulation signal) from the external device, the corresponding first information and second information, and time information of the external device. Data processing device 100 receiving from operation processing unit 420 first image 41 and second image 42 processed as one image may simply cause display 300 to display the processed one image.

The external device is either one of a device relating to visual stimulation (visual stimulation signal processing device 600) and a device which detects a vital sign of subject 2. Operation processing unit 420 can thus obtain relevant data of the external device necessary for appropriate diagnosis of vertigo together.

Ocular movement data processing system 10 according to the first embodiment is a system that processes ocular movement data in an equilibrium examination. Ocular movement data processing system 10 comprises imaging device 400 that captures an image of an eyeball of subject 2, data processing device 100 that receives data from imaging device 400 and processes the data, and an external device (visual stimulation signal processing device 600 and additional device 700) that obtains at least one of information about subject 2 and information about an equilibrium examination. Imaging device 400 includes housing 401 mounted on the head of subject 2, an imaging unit (first imaging unit 411 and second imaging unit 412) that is held by housing 401 and captures an image of the eyeball of subject 2, operation processing unit 420 (a communication unit) that communicates information with the external device, and operation processing unit 420 (a control unit) that synchronizes together the image captured by the imaging unit (first imaging unit 411 and second imaging unit 412) and an external signal received from the external device. Data processing device 100 includes control unit 120 (a receiving unit) that receives the synchronized first and second images from imaging device 400, and control unit 120 (a processing unit) that subjects the received, synchronized first and second images to prescribed data processing.

A method for control by imaging device 400 according to the first embodiment comprises the steps of: causing the imaging unit (first imaging unit 411 and second imaging unit 412) to capture an image of an eyeball of subject 2; receiving an external signal from an external device; and synchronizing together the image captured by the imaging unit (first imaging unit 411 and second imaging unit 412) and the external signal received from the external device.

Second Embodiment

For ocular movement data processing system 10 according to the first embodiment is described a configuration in which first image 41 captured by first imaging unit 411, second image 42 captured by second imaging unit 412, and information of an external device (visual stimulation signal processing device 600 and additional device 700) are synchronized together in imaging device 400. For an ocular movement data processing system according to a second embodiment will be described a configuration to further synchronize information of a sensor provided to imaging device 400.

Figure 15:
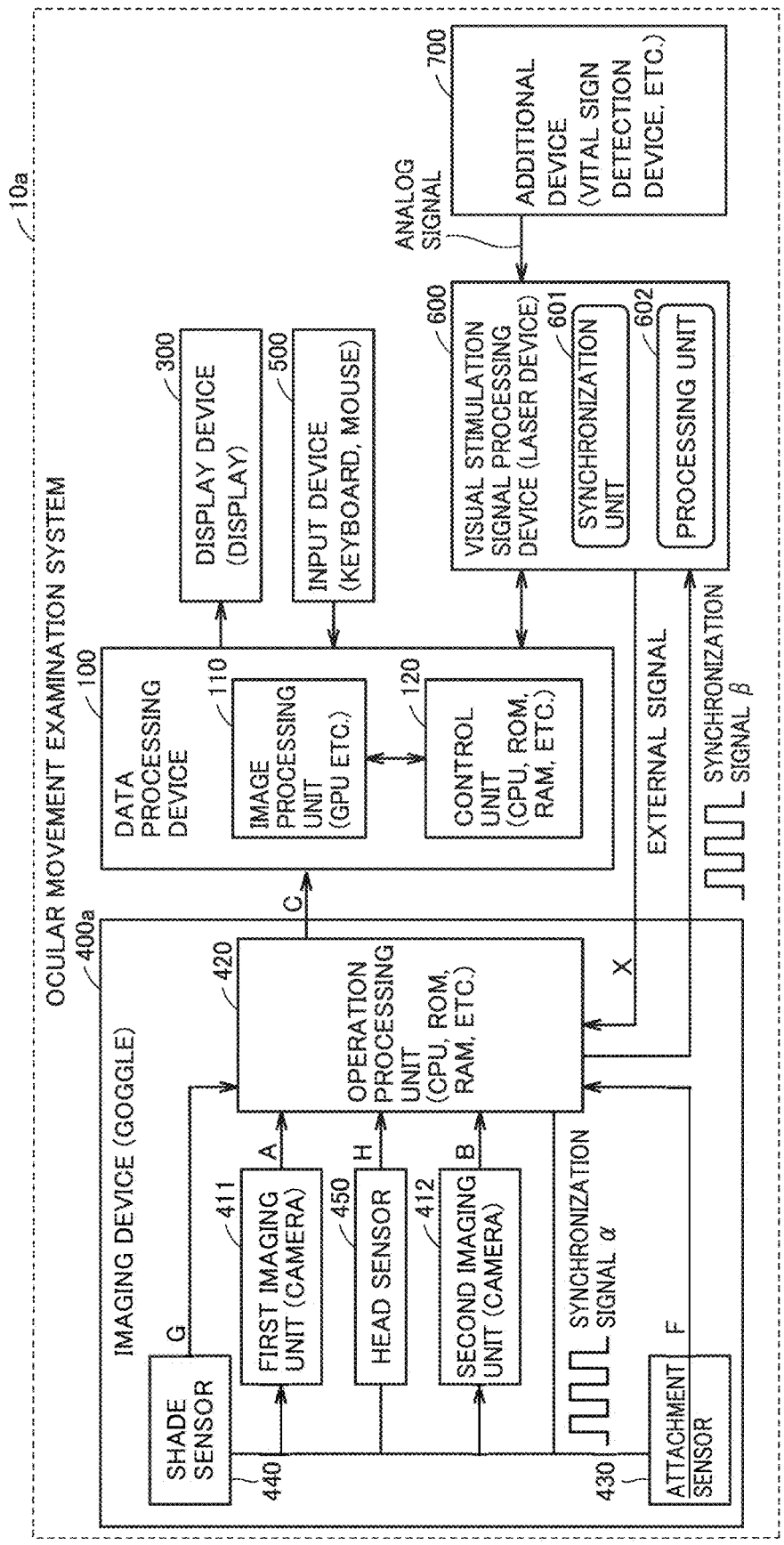
FIG. 15 is a block diagram generally showing a configuration of an ocular movement data processing system according to a second embodiment.

FIG. 15 is a block diagram generally showing a configuration of an ocular movement data processing system 10a according to the second embodiment. Ocular movement data processing system 10a shown in FIG. 15 is the same in configuration as ocular movement data processing system 10 shown in FIG. 3 except that how an imaging device 400a is configured. Accordingly, any configuration in the FIG. 15 ocular movement data processing system 10a that is identical to that of the FIG. 3 ocular movement data processing system 10 is identically denoted and will not be described specifically.

In imaging device 400a, as shown in FIG. 15, image data A from first imaging unit 411 and image data B from second imaging unit 412 are processed in operation processing unit 420 and transmitted to data processing device 100 as image data C. First imaging unit 411 includes an infrared imaging device, and a processing circuit (not shown) that attaches information of a frame number and a time stamp (first information) to an image that is captured by the infrared imaging device for each frame to provide image data A and output image data A to operation processing unit 420. The information included in the first information is not limited to a frame number and a time stamp, and may be information of at least one of the frame number and the time stamp, and may include information such as a frame rate, an amount of exposure, and a contrast. Similarly, second imaging unit 412 includes an infrared imaging device, and a processing circuit (not shown) that attaches information of a frame number and a time stamp (second information) to an image that is captured by the infrared imaging device for each frame to provide image data B and output image data B to operation processing unit 420. The information included in the second information is not limited to a frame number and a time stamp, and may be information of at least one of the frame number and the time stamp, and may include information such as a frame rate, an amount of exposure, and a contrast. The first information and the second information are also referred to as information provided for a captured image.

Imaging device 400a includes, in addition to first and second imaging units 411 and 412, an attachment sensor 430 that senses an attached state of housing 401 to subject 2, a shade sensor 440 that senses a shaded state of first and second imaging units 411 and 412, and a head sensor 450 that senses how subject 2 moves his/her head, how the subject orients his/her head, in particular, in housing 401. Attachment sensor 430 is, for example, a contact sensor, and when the contact sensor issues an OFF signal, operation processing unit 420 can determine that housing 401 of imaging device 400a is detached from the head of subject 2 or displaced from a prescribed position. Shade sensor 440 is, for example, an optical sensor, and when shading cover 402 is attached and imaging device 400a is internally dark, the optical sensor issues an OFF signal, and operation processing unit 420 can determine that first and second imaging units 411 and 412 are shaded. Head sensor 450 is composed of an acceleration sensor, an angular velocity sensor, and a geomagnetic sensor each provided for directions along three axes for a total of nine sensors. The acceleration sensor can sense the posture of the head of subject 2 by sensing gravitational acceleration. The angular velocity sensor can sense the angular velocity of the head of subject 2. The geomagnetic sensor can sense the orientation (or azimuth) of the head of subject 2. Operation processing unit 420 calculates head angle, head angular velocity and the like through an operation based on a measurement signal received from head sensor 450. While for imaging device 400a will be described a configuration in which attachment sensor 430, shade sensor 440, and head sensor 450 are all provided, at least one of attachment sensor 430, shade sensor 440, and head sensor 450 may be provided. As a matter of course, imaging device 400a may be provided with sensors other than attachment sensor 430, shade sensor 440, and head sensor 450.

For imaging device 400a, the signals from attachment sensor 430, shade sensor 440, and head sensor 450 are also synchronized with the images captured by first and second imaging units 411 and 412. Specifically, as a method in which imaging device 400a synchronizes an image captured by first imaging unit 411, an image captured by second imaging unit 412, and the signals received from attachment sensor 430, shade sensor 440 and head sensor 450 together, there is a method, for example, of synchronization based on time stamps added to the images and the signals received from the sensors. The time stamps are generated based on the times counted by the counters of first imaging unit 411, second imaging unit 412, attachment sensor 430, shade sensor 440, and head sensor 450, and in order to use the images and the signals received from the sensors for synchronization, it is necessary to synchronize the times counted by the counters. In order to synchronize the times counted by the counters of the imaging units and sensors, operation processing unit 420 transmits synchronization signal α to each of first imaging unit 411, second imaging unit 412, attachment sensor 430, shade sensor 440, and head sensor 450.

Based on synchronization signal α, first imaging unit 411, second imaging unit 412, attachment sensor 430, shade sensor 440, and head sensor 450 synchronize and thus adjust the time counted by each counter, and add a time stamp to each image and each sensor's signal. Based on each time stamp adjusted by synchronization signal α, operation processing unit 420 can reliably synchronize the image captured by first imaging unit 411, the image captured by second imaging unit 412, and the signals from attachment sensor 430, shade sensor 440, and head sensor 450 together to obtain a right eye image, a left eye image, and each sensor's signal of the same timing.

Operation processing unit 420 may not provide synchronization based on the time stamp added to each image and each sensor's signal, and may instead provide synchronization based on other information (e.g., a frame number, a number, etc.) added to each image and each sensor's signal. Further, operation processing unit 420 may not transmit synchronization signal α to each of first imaging unit 411, second imaging unit 412, attachment sensor 430, shade sensor 440, and head sensor 450, and, for example, may instead synchronize the time counted by each counter, as timed when each imaging unit and each sensor are powered on. Further, attachment sensor 430, shade sensor 440, and head sensor 450 may output a result of sensing to operation processing unit 420, as timed by synchronization signal α, without adding information such as a time stamp.

Figure 16:
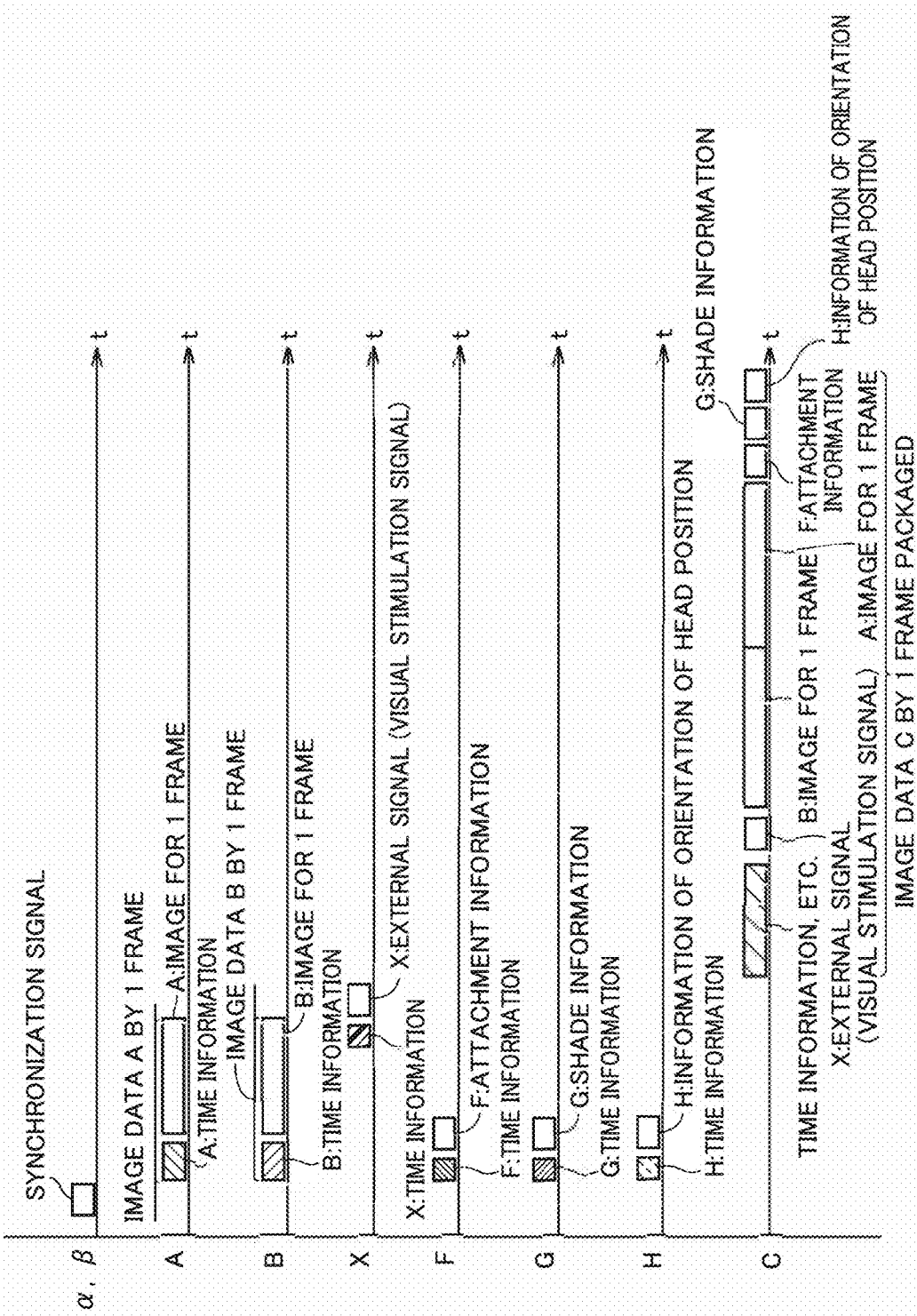
FIG. 16 is a schematic diagram representing image data of each of a first imaging unit and a second imaging unit, signals from sensors, and image data output by an operation processing unit.

Operation processing unit 420 outputs each image and each sensor's signal that are synchronized together to data processing device 100. FIG. 16 is a schematic diagram representing image data of each of first imaging unit 411 and second imaging unit 412, signals from sensors, and image data output by operation processing unit 420. As shown in FIG. 16, first imaging unit 411 adds time information (a frame number, a time stamp, etc.) to an image of one frame and outputs the image with the time information as image data A. Similarly, as shown in FIG. 16, second imaging unit 412 adds time information (a frame number, a time stamp, etc.) to an image of one frame and outputs the image with the time information as image data B. Visual stimulation signal processing device 600 adds time information (a number, a time stamp, etc.) to the visual stimulation signal and outputs the visual stimulation signal with the time information as data X.

As shown in FIG. 16, attachment sensor 430 adds time information (such as a time stamp) to attachment information (for example, an ON signal or an OFF signal) including a result of sensing, and outputs the attachment information with the time information as data F. As shown in FIG. 16, shade sensor 440 adds time information (such as a time stamp) to shade information (for example, an ON signal or an OFF signal) including a result of sensing, and outputs the shade information with the time information as data G. As shown in FIG. 16, head sensor 450 adds time information (such as a time stamp) to information in orientation of the head (e.g., a measurement signal) including a result of sensing, and outputs the information with the time information as data H. As shown in FIG. 16, operation processing unit 420 processes the image of one frame of first imaging unit 411 and the image of one frame of second imaging unit 412 including the same time information as one image, and outputs the processed image, data X of visual stimulation signal processing device 600, the time information, data F of attachment sensor 430, data G of shade sensor 440, and data H of head sensor 450 as one image data C.

As described above, imaging device 400a according to the second embodiment further comprises head sensor 450 (a first detection unit) that is held by housing 401 and senses movement of the head of subject 2, and operation processing unit 420 synchronizes together a first image captured by first imaging unit 411, a second image captured by second imaging unit 412, an external signal (a visual stimulation signal) from an external device, and a result of sensing (a measurement signal) by head sensor 450. Thus, imaging device 400a can accurately grasp an external signal received from the external device and a movement of the head of subject 2, that are obtained at a time when first and second imaging units 411 and 412 capture images, and thus allows appropriate diagnosis.

Further, the attachment sensor 430 that is held by housing 401 and senses an attached state of housing 401 is further comprised and operation processing unit 420 synchronizes together the first image captured by first imaging unit 411, the second image captured by second imaging unit 412, the external signal (the visual stimulation signal) from the external device, and a result of sensing (an ON signal or an OFF signal) by attachment sensor 430. Thus, imaging device 400a can accurately grasp an external signal received from the external device and an attached state of imaging device 400a, that are obtained at a time when first and second imaging units 411 and 412 capture images, and thus allows appropriate diagnosis.

Further, the shade sensor 440 that is held by housing 401 and senses a shaded state of a portion imaged by first imaging unit 411 and a shaded state of a portion imaged by second imaging unit 412 is further comprised, and operation processing unit 420 synchronizes together the first image captured by first imaging unit 411, the second image captured by second imaging unit 412, the external signal (the visual stimulation signal) from the external device, and a result of sensing (an ON signal or an OFF signal) by shade sensor 440. Thus, imaging device 400a can accurately grasp an external signal received from the external device and a shaded state of the imaging unit, that are obtained at a time when first and second imaging units 411 and 412 capture images, and thus allows appropriate diagnosis.

Modified Example

In the first embodiment, first and second images 41 and 42 are included in image data C as one image and thus output. However, image data C output by imaging device 400 is not limited as shown in FIG. 4, that is, to a configuration in which an image of one frame of first imaging unit 411 and an image of one frame of second imaging unit 412 including the same time information are processed as one image, and the processed image and the time information of first and second imaging units 411 and 412 are output as one image data C. For example, imaging device 400 may alternately dispose image data A of first imaging unit 411, image data B of second imaging unit 412 and an external signal received from an external device that include the same time information, and imaging device 400 may output the same as image data C.

FIG. 17 is a schematic diagram for illustrating an image of first imaging unit 411 and that of second imaging unit 412 alternately disposed to output image data. As shown in FIG. 17, operation processing unit 420 alternately disposes data X of visual stimulation signal processing device 600, and image data A of first imaging unit 411 and image data B of second imaging unit 412 that include the same time information to package them into image data C and thus outputs image data C. An image of one frame of first imaging unit 411 and an image of one frame of second imaging unit 412 including the same time information are not processed as one image; rather, image data A and B and the external signal from the external device are simply packaged into one image data C and output. While in the example shown in FIG. 17 the time information of first imaging unit 411, the time information of second imaging unit 412 and the time information of the external device are separately output, the time information of first imaging unit 411, the time information of second imaging unit 412 and the time information of the external device may be combined into one and thus output.

The modified example shown in FIG. 17 is also similarly applicable to image data C output by imaging device 400a according to the second embodiment.

As described above, operation processing unit 420 of the modified example alternately transmits image data A and image data B with a first image and a second image synchronized together. This ensures that data processing device 100 receives the synchronized image data A and B, and providing the synchronized images to operator 1 allows an appropriate diagnosis of vertigo to be made.

Although the present disclosure has been described and illustrated in detail, it is clearly understood that the same is by way of illustration and example only and is not to be taken by way of limitation. The scope of the present disclosure is interpreted by the terms of the appended claims, and any modification within the meaning and scope equivalent to the terms of the claims is intended to be encompassed.

The invention claimed is:

1. An imaging device that captures an image of an eyeball in an equilibrium examination, comprising:
a housing that is mounted on a head of a subject;
a camera that is held by the housing and captures a first image of a first eyeball of the subject and a second image of a second eyeball of the subject as image data;
communication circuitry configured to communicate information with a first external device which is an external stimulation device and a second external device which is an external vital sign sensor device; and
controller circuitry configured to:
synchronize the image data captured by the camera with external signals output from the first and second external devices and received by the communication circuitry as synchronized data using time stamp information and synchronization signals when both image data and external signals are received by the controller circuitry during a predetermined period, and
transmit the synchronized data to a third external device which is an external processing device together in a packaged manner.

2. The imaging device according to claim 1, wherein the controller circuitry is further configured to transmit a synchronization signal to the camera and the first and second external devices.

3. The imaging device according to claim 2, wherein the synchronization signal, transmitted to the camera and the first and second external devices, is periodically repeated.

4. The imaging device according to claim 1, wherein the communication circuitry is further configured to alternately output the image data as first image data and second image data with the first image and the second image synchronized together.

5. An ocular movement data processing system that processes ocular movement data in an equilibrium examination, comprising:
an imaging device that captures a first image of a first eyeball of a subject and a second image of a second eyeball of the subject as image data;
a data processing device that receives the image data from the imaging device and processes the image data as the ocular movement data; and
a first external device which is an external stimulation device and a second external device which is an external vital sign sensor device that obtains first information about the subject and second information about the equilibrium examination,
wherein the imaging device includes:
a housing that is mounted on a head of the subject;
a camera that is held by the housing;
communication circuitry configured to communicate information with the external stimulation device and the external vital sign sensor device; and
controller circuitry configured to:
synchronize together the image data captured by the camera and external signals output from the first and second external devices and received by the communication circuitry as synchronized data using time stamp information and synchronization signals when both image data and external signals are received by the controller circuitry during a predetermined period, and
transmit the synchronized data to a third external device which is an external processing device together in a packaged manner.

6. A method for controlling implemented by an imaging device that captures a first image of a first eyeball of a subject and a second image of a second eyeball of the subject as image data in an equilibrium examination, the imaging device including: a housing that is mounted on a head of a subject, and a camera that is held by the housing, the method comprising:

causing the camera to capture the first image of the first eyeball of the subject and the second image of the second eyeball of the subject as image data;

receiving external signals from a first external device which is an external stimulation device and a second external device which is an external vital sign sensor device;

synchronizing together the image data captured by the camera and the external signals received from the first and second external devices as synchronized data using time stamp information and synchronization signals when both image data and external signals are received during a predetermined period; and transmitting the synchronized data to a third external device which is an external processing device together in a packaged manner.

7. The method according to claim 6, further comprising: adding information, designated for each captured image, to the image data.

8. The method according to claim 7, wherein transmitting a synchronization signal to the camera and the first and second external devices.

9. The method according to claim 8, further comprising periodically repeating the synchronization signal transmitted to the camera and the first and second external devices.

10. The method according to claim 7, further comprising alternately outputting first image data and second image data with the first image and the second image synchronized together.

11. The method according to claim 7, further comprising processing the first image and second image as one image, and transmitting, to the external data processing device, image data including the image obtained through processing, first information and second information corresponding to the image, and the external signals output from the first and second external devices.

\* \* \* \* \*